(12) United States Patent
Day et al.

(10) Patent No.: US 8,709,341 B2
(45) Date of Patent: Apr. 29, 2014

(54) SYSTEM FOR PURIFYING AIR THROUGH GERMICIDAL IRRADIATION AND METHOD OF MANUFACTURE

(75) Inventors: Edwin David Day, Calgary (CA); Bernard K Deschner, Calgary (CA)

(73) Assignee: Morphic Envirotech Inc., Calgary (CA)

( * ) Notice: Subject to any disclaimer, the term of this patent is extended or adjusted under 35 U.S.C. 154(b) by 460 days.

(21) Appl. No.: 12/820,011

(22) Filed: Jun. 21, 2010

(65) Prior Publication Data

US 2010/0260644 A1     Oct. 14, 2010

Related U.S. Application Data

(63) Continuation of application No. 11/835,899, filed on Aug. 8, 2007, now abandoned.

(51) Int. Cl.
| | |
|---|---|
| *A61L 2/00* | (2006.01) |
| *A62B 7/08* | (2006.01) |
| *A61L 9/00* | (2006.01) |
| *A61L 9/01* | (2006.01) |
| *B01J 21/08* | (2006.01) |
| *A61L 9/014* | (2006.01) |
| *A61L 9/20* | (2006.01) |
| *B01D 53/34* | (2006.01) |
| *B01D 24/04* | (2006.01) |
| *B01D 24/00* | (2006.01) |
| *B01J 35/00* | (2006.01) |
| *B01J 21/06* | (2006.01) |
| *F24F 13/28* | (2006.01) |

(52) U.S. Cl.
CPC .. *A61L 9/00* (2013.01); *A61L 9/014* (2013.01); *A61L 9/20* (2013.01); *A61L 9/205* (2013.01); *B01D 53/34* (2013.01); *B01D 24/04* (2013.01); *B01D 24/001* (2013.01); *B01J 35/004* (2013.01); *B01J 21/063* (2013.01); *F24F 13/28* (2013.01)

USPC ...... 422/24; 422/1; 422/5; 422/120; 422/186; 422/186.3; 424/76.8; 424/77; 502/242; 502/250; 502/253; 502/248

(58) Field of Classification Search
CPC ............ A61L 9/00; A61L 9/014; A61L 9/20; A61L 9/205; B01D 53/34; B01D 24/04; B01D 24/001; B01J 35/004; B01J 21/063; F24F 13/28
USPC ................ 96/149, 224; 424/76.8, 77; 53/285; 422/1, 24, 120, 186, 186.3; 502/242, 502/250, 253, 248

See application file for complete search history.

(56) References Cited

U.S. PATENT DOCUMENTS

| | | | |
|---|---|---|---|
| 2003/0026585 A1* | 2/2003 | Iimura | 385/144 |
| 2004/0265587 A1* | 12/2004 | Koyanagi et al. | 428/398 |

* cited by examiner

*Primary Examiner* — Monzer R Chorbaji
(74) *Attorney, Agent, or Firm* — Sean W Goodwin

(57) ABSTRACT

An air purifying system includes one or more air permeable photocatalytic elements defining a core cavity having a sealed top end and an open bottom end. A sealed air flow path ensures that air travels from an outside of the core cavity, through the one or more photocatalytic elements, into the core cavity, to be expelled through the open bottom end. A UV radiation source disposed within the core cavity irradiates air travelling along the sealed flow path and an interior of the one or more photocatalytic elements. Each photocatalytic element is manufactured using a substrate, that is conductive of and transparent to UV radiation, coated with a photocatalyst. A non-photocatalytically active material is initially coated on the substrate and is then converted to a photocatalyst by calcination.

9 Claims, 15 Drawing Sheets

(a)          (b)

(c)          (d)

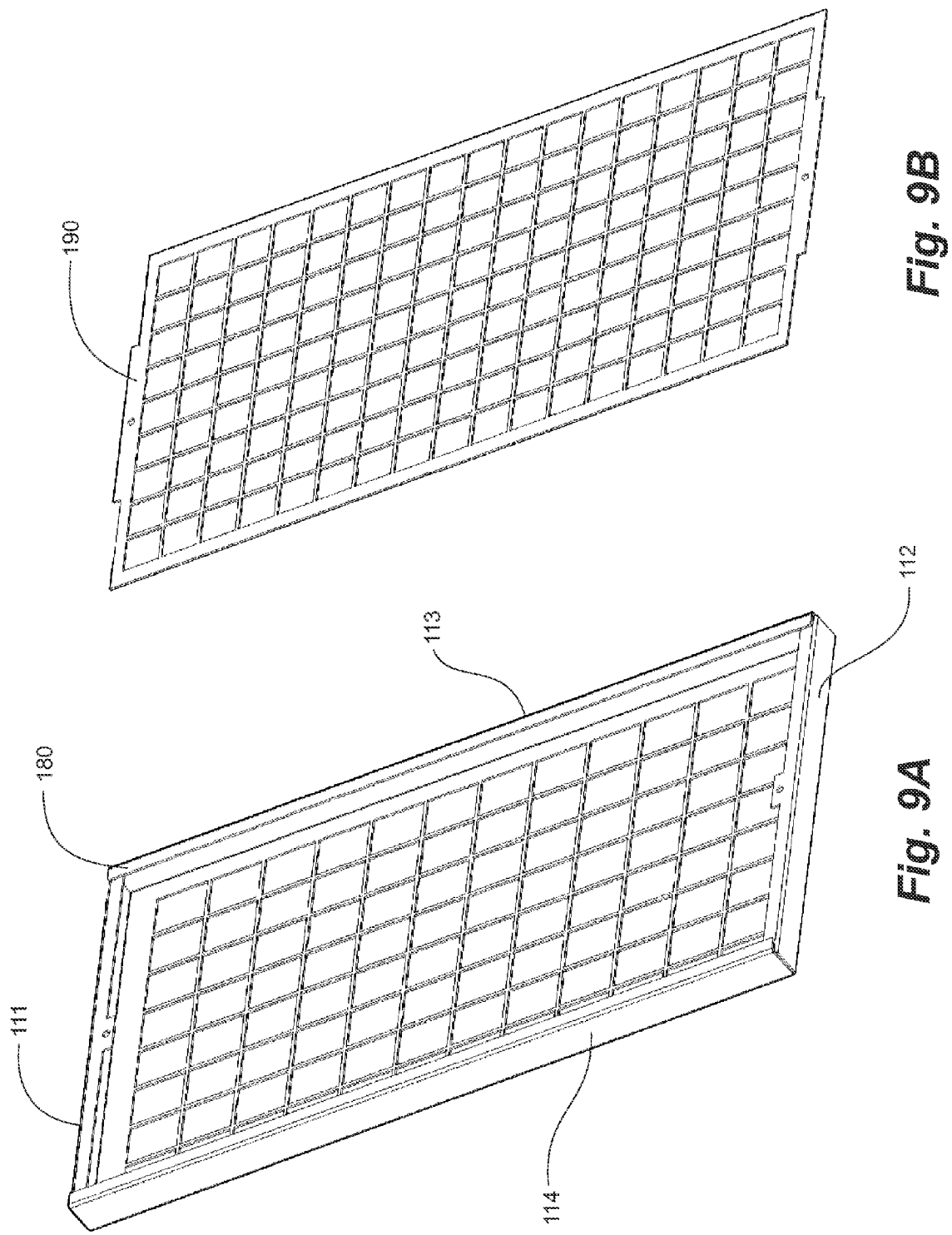

SYSTEM FOR PURIFYING AIR THROUGH GERMICIDAL IRRADIATION AND METHOD OF MANUFACTURE

CROSS-REFERENCE TO RELATED APPLICATIONS

This application is a Continuation-In-Part of U.S. patent application Ser. No. 11/835,899, filed on Aug. 8, 2007, published as US 2009/0041632 on Feb. 12, 2009, and now abandoned, the entirely of which is incorporated fully herein by reference.

BACKGROUND OF THE INVENTION

The present invention relates to a system and method of manufacturing the same, for efficiently purifying indoor air by combining forced (variable speed) air movement (fan and motor), filtration, ultraviolet germicidal irradiation, and photocatalysis in an air purifier unit.

Some of the earliest published references to titania (titanium dioxide or $TiO_2$) photocatalysts are by Formenti, M., et al., "Heterogeneous Photocatalysis for Oxidation of Paraffins", Chemical Technology 1, 680-686, 1971 and U.S. Pat. No. 3,781,194 issued Dec. 25, 1973. Since the 1972 discovery of the photocatalytic splitting of water on titanium dioxide electrodes, by Fujishima and Honda, the science and technology related to heterogeneous photocatalysis in both water and air has been extensively studied and is the subject of numerous patents and scientific publications. Both the physics and chemistry of heterogeneous photocatalysis remain areas of active investigation. Much of the early work of relevance to this patent is summarized, by Kittrell in U.S. Pat. Nos. 6,179,972 and 6,221,259, as well as, Peill, et al., in U.S. Pat. Nos. 5,875,384 and 6,051,194. Despite investigation of many alternatives, the anatase crystal morphology of titanium dioxide remains the photocatalytically active semi-conductor of economic choice, although many claims of additive enhancements have been and continue to be made.

Considerable historical effort has been expended to maximize photocatalytic activity of anatase $TiO_2$ by minimizing particle size (to maximize effective surface area) while maintaining strong adhesion to substrate surfaces. It is well known and documented that photocatalytic activity is directly related to (a) the intensity and wavelength of irradiation at the illuminated photocatalyst surface area, (b) the magnitude of the illuminated photocatalyst surface area, (c) the rate of flow of contaminants across the illuminated photocatalyst surface area (irradiated surface contact), and (d) in air, the "absolute" humidity of the ambient air. The "quantum or photocatalytic efficiency" relates to the fraction of light-source photons that are effective in causing the photocatalyzed reactions.

Considerable effort is currently being expended, in the field of photocatalysis, to enhance the photocatalytic efficiency of anatase titanium dioxide with various catalytic additives (as described in many of the patents cited, e.g., U.S. Pat. Nos. 6,409,928, 6,179,972, and 6,221,259) and to extend the wavelength of photocatalyst-activating irradiation into the visible wavelength range, as described in U.S. Pat. Nos. 7,153,808 and 7,175,911.

The objective of the present invention is to provide a large illuminated photocatalyst surface area while ensuring intimate air-surface contact, at all air flow rates, so as to maximize the photocatalytic efficiency of the light source. Where the photocatalyst substrate fibers are high-purity quartz, wool, mat, or felt, the fibers act as elementary waveguides having a UV-conductive core with a reactive outer coated surface. Refraction and reflection (both internal and external) of randomly oriented fibers ensure efficient distribution of light photons throughout the fiber mass, until absorption at the photocatalytic coating occurs.

Early work with photocatalyst powder coatings encountered particle size minimization and bond-to-substrate issues. Various high temperature coating application techniques have been technically successful but are economically and practically prohibitive for coating fiber wool, mat, or felt. Organic binders for powders, such as methylmethacrylate and various organic resins, have been found to emit unacceptable odors under UV-C irradiation. Titanium oxide films formed by inorganic peroxotitanium hydrate sol gels together with a peroxotitanic acid binder have been found to have good substrate-bonding and photocatalytic properties, while remaining odor-free under UV-C irradiation.

Photocatalyzed reactions of volatile compounds (VCs) are known to be strongly endothermic, such that the photocatalyst-activating energy output of commonly available lamps limits the concentrations of treatable airborne VCs to parts-per-million (ppm) or less. The concentrations of most noxious/offensive odors and airborne pathogens are within this treatable range.

U.S. Pat. No. 5,330,722 discloses, in one embodiment, a longitudinal arrangement of a disposable, hollow, cylindrical air filter rotated about the longitudinal axis between two closely spaced UV lamps (one irradiating the inside wall and one irradiating the outside wall. Electrostatic but no photocatalytic enhancement is claimed. Air flow, as in the present invention, is from the outside to the interior (core cavity) of the filter cylinder. The germicidal filter medium is claimed to include fibrous materials (including fiberglass) and pleated paper suitable for use in filtering air. The ultraviolet radiation sources claimed include ozone producing lamps. There is no discussion of UV-induced deterioration of filter materials.

U.S. Pat. No. 5,616,172 discloses a longitudinal but rectangular arrangement of UV lamps within the enclosed housing of an air treatment system. There is neither photocatalytic activity nor disposable cartridge claimed.

U.S. Pat. Nos. 5,779,912 and 6,409,928 disclose a photocatalytic method and apparatus for mineralizing organic contaminants in water or air. The photocatalytic performance is claimed to be enhanced by addition of an oxidant stream to the contaminated fluid stream as well as addition of metal catalysts to the photocatalyst coatings. With some similarities to the present invention in concept, the differences are: (a) the focus of these patents upon contaminated water, (b) the photocatalyst coating is applied only to the directly irradiated surface, and (c) a supplementary oxidant (oxygen or ozone) stream is directed to the reaction zone. Many reasons are stated for rejecting an annular photo-reactor concept, such as the present invention.

U.S. Pat. No. 5,833,740 discloses a longitudinal, coaxial combination of UV-V and UV-C light sources within the enclosed housing of a chemical and biological air purifier. There is neither photocatalytic activity nor a disposable cartridge claimed.

U.S. Pat. Nos. 5,875,384 and 6,051,194 disclose the construction and performance characteristics of oriented $TiO_2$-coated fiber optic cable reactors (FOCRs) and their use in the degradation of organic and inorganic pollutants in both air and water. The fibers described were 400 to 1,000 microns in diameter and were maintained straight and parallel within the reactor. Photocatalyst particles were baked onto the fiber surfaces after dipping into a $TiO_2$ slurry. Due to weak photocatalyst-fiber bonding, there was a concern for de-lamination of the coating on fiber-to-fiber contact. Therefore, spacers were utilized to prevent fiber-to-fiber contact. The UV light source was unspecified.

U.S. Pat. No. 5,997,619 discloses an annular filter arrangement preceding UV germicidal irradiation. No photocatalysis is claimed.

U.S. Pat. No. 6,053,968 discloses an annular portable room air purifier in which the germicidal UV lamps are arranged at the outer periphery of the core cavity, not on the longitudinal axis. HEPA filtration but not photocatalysis is claimed.

U.S. Pat. Nos. 6,179,972 and 6,221,259 disclose a two-stage process, catalyst, and apparatus for photocatalytic conversion of contaminants in oxygen-containing air and water streams combining a UV-activated photocatalysis stage and a subsequent high temperature catalysis stage. The photocatalyst is described as including various combinations of titanium and zirconium, both supported by silica "gel".

U.S. Pat. Nos. 6,235,401, 6,344,277, 6,344,278, and 6,379,811 disclose the method of preparation of a yellow transparent jelly (viscous) amorphous type titanium peroxide sol which serves as an excellent binder for titanium dioxide powders and sol gels. These patents further teach that when the titanium peroxide sol is heated at 100 degrees C. or more for several hours, the anatase type of titanium oxide sol is obtained. When a substrate is coated with the amorphous type titanium peroxide sol and then dried and heated at 250 to 940 degrees Celsius, an anatase type of titanium dioxide is obtained. This material is similar to the preferred photocatalyst material of the present invention (without the necessity of heating).

U.S. Pat. No. 6,309,611 discloses a multi-stage photocatalytic reactor for both gaseous and aqueous streams, each stage of which is somewhat similar in concept to the present invention with the following differences:
1. The air flow through the photocatalytic medium is reversed (out from the illuminated side as opposed to into the illuminated side).
2. There is no described pre-filtration.
3. The preferred photocatalytic medium substrate is a cellulosic-fiber fabric material (cotton or any bio-polymeric) to which the titania particles are claimed to be hydrogen bonded in a flexible stocking or a rigid metallic or ceramic screen.

U.S. Pat. No. 6,309,611 provides an excellent background discussion of prior relevant art, patents, UV light sources, mass transfer considerations, photocatalytic media, and provides an internal classification (by type) of catalytic media.

U.S. Pat. No. 6,358,374 discloses an elaborately schematic integrated photocatalytic gas purifier and an adsorbent bed (gaseous contaminant accumulator). The contaminants are first adsorbed (accumulated/concentrated) in the bed until saturated. The adsorbent bed is then regenerated by heating to release the captured contaminants which are released into a fixed volume of gas that is re-circulated through the heated bed and through a photocatalytic gas purifier which oxidizes the released contaminants. Unfortunately, the patent discloses no details of the photocatalytic gas purifier, light source, or photocatalyst.

WO/2002/004036 discloses a method and apparatus for air purification that consists of a cylindrical arrangement of an inner number of UV light sources (illumination section), preceded by pre-filters (pre-sterilization section). An antimicrobial agent may be coated on surfaces in one or both the filter and illumination sections. Design-induced turbulence is claimed to increase the dwell time of contaminants in the illumination section. However, dwell time is determined by flow rates, not turbulence. Turbulence does increase the possibility of surface contact. No photocatalysis is claimed.

U.S. Pat. No. 6,358,374 discloses a method for preparing a thin film of oriented anatase crystals on a substrate by spraying a vaporized titanium alkoxide (in an inert carrier gas) onto the heated substrate surface, at atmospheric pressure. This method and process is not used in the present invention.

U.S. Pat. Nos. 6,228,502 and 6,465,042 disclose a chemical vapor deposition technique for producing an oriented crystalline film of anatase titanium dioxide on a substrate surface, followed by annealing in an oxygen atmosphere, and then coating with silver, or copper, or oxide thereof.

WO/2002/083307 discloses an annular photocatalytic air purifier comprising: (a) a tubular housing having an inner and an outer wall, a central axis, a first end having a centrally located air intake nozzle, a second end having at least one air exhaust port; (b) an air exhaust plenum between the inner housing wall and a radial porosity medium, the porosity medium extending radially and axially about the axis; and (c) a housing central portion defined by an interior perimeter of the radial porosity medium, the central housing enclosing an ultraviolet lamp and a packing medium, the packing medium extending radially and axially about the lamp and comprising a plurality of spiral wound filaments (semi-transparent to UV light, E-glass, a form of fiberglass, and of 15-25 microns diameter) coated with a photocatalytic film. The substrate/support fibers are claimed to be any of glass, metal, plastic, nylon, or other material that can be assembled into small fibers. Such fibers are claimed to be organized into a twisted strand "bottle brush" configuration, bound by at least one stainless steel wire. Although geometrically similar to the present invention, the major differences are:
1. No pre-filtration is claimed, in contrast with the present invention.
2. The fiber orientation is regular ("bottle brush"), not random (wool, felt, mat), as in the present invention.
3. The fibers are, at best, semi-transparent to long wavelength UV light and opaque to short wavelength UV (germicidal) and not fully transparent, as in the present invention.
4. The direction of air flow is inside-out, not outside-in.

WO/2002/102497 discloses a photocatalytic air purifier apparatus that consists of an annular arrangement of an inner photocatalyst-coated transparent sleeve ("member") enclosing the axial UV light source with both enclosed by either a photocatalytic cylindrical surface or "a plurality of tubes". Air flow is directed through the annulus between the transparent sleeve and the outer photocatalytic cylinder. Photocatalytic activity is limited by the smaller UV-illuminated photocatalyst-coated surface area and lesser intimate contact between airborne molecules and the smaller photocatalyst surface than in the present invention.

U.S. Pat. No. 6,531,100 discloses various metal wire mesh, cloth, and non-woven substrates, surface enhanced with particles of many materials bound to the substrate surface, on coating with photocatalyst, to maximize the area presented to a UV light source. Baking or sintering, after wet application of photocatalyst sol, is said to provide a secure photocatalyst bond to the substrate material. The patent also describes various arrangements of planar photocatalyst-supporting bodies and UV light sources in photocatalytic apparatus.

U.S. Pat. No. 6,589,489 discloses an air purifier of similar geometry to the present invention but incorporating a "dielectric body" in place of the photocatalytic cartridge of claim 1 and utilizes both UV1 (UV-V) and UV2 (UV-C) light. In this invention, the dielectric body may be made of, for example, quartz, or alumina fibers or silica granules or sponge so that it is porous to air and transmissive to UV light. The dielectric body of this invention may contain photocatalytic material and electron transfer is claimed to be enhanced by and electric field imposed by concentric anode and cathode metal mesh cylinders incorporated within the dielectric body. Air flow is from the inside→out (of the dielectric body) in contrast with the flow from the outside→in (of the photocatalytic cartridge) in the present invention.

U.S. Pat. No. 6,602,918 discloses processes for producing titanium oxide coating agents for the purpose of forming a titanium oxide film on a substrate with improved adhesion and increased density. The product of this invention is very similar to that used in the present invention.

U.S. Pat. No. 6,730,265 discloses an air UV disinfection device and method involving a UV light source connected by fiber optics to a gas purification zone (reaction chamber of gas purifier) that may involve reflective or photocatalyst-coated interior surfaces. This patent also claims "particle arresters" (fiber filters) composed of fibers selected from the group consisting of glass fibers, acrylic fibers, quartz fibers, paper fibers, cellulose fibers, cotton fibers, plastic fibers, and cominations thereof. Gas flow and control of that flow through the gas purification zone is not detailed.

U.S. Pat. No. 6,602,918 discloses a small (suitable for plugging directly into an electrical outlet) apparatus and method for purifying air consisting of a chimney, UV light source, a doped (platinum metal, etc.) photocatalyst (primarily titanium dioxide) coated on internal walls or fibrous mass (unspecified). Air flow through the unit is maintained by convection created by internal heating. Convection alone is a slow process that generates a small number of air exchanges per hour in even modest-sized indoor environments.

U.S. Pat. No. 6,764,655 discloses a light-leakage type photocatalytic filter comprised of longitudinally bundled photocatalyst fibers with inter-fiber gaps to permit fluid communication pathways. Light introduced at the ends of the fibers travels along the photocatalyst fibers while partially leaking therefrom and thus causing photocatalytic reactions. According to the patent, fluid flow may be parallel, perpendicular, or inclined with respect to the longitudinal direction of the fiber bundle. A bundle consists of about 10,000 fibers of 125 nm in diameter and 200 mm in length. Neither the photocatalyst nor the composition of the fibers is disclosed.

U.S. Pat. No. 6,773,683 discloses a schematic concept for photocatalytically oxidizing sulfur dioxide to sulfur trioxide using a UV laser or lamp light source connected, via fiber bundles, to a reactor but without disclosure of photocatalyst or details of reactor design.

U.S. Pat. No. 6,783,578 discloses an air purification apparatus that includes a HEPA or ULPA cartridge filter and UV lamp configuration, geometrically similar to the present invention but without a photocatalytic medium and with the air flow reversed (from the inside of the cartridge to the outside).

U.S. Pat. No. 6,835,679 discloses a method and apparatus for light curing of composite materials incorporating one or more "lossy" optical fibers. This patent teaches that optical fibers may be made lossy by bending the fiber, weaving the fiber into a mat (to create periodic micro bends), or by removing the fiber cladding. Such light losses (leakage) distribute the light throughout the composite material.

U.S. Pat. No. 6,884,399 discloses a modular photocatalytic air purifier intended for installation in heating, ventilating, and air conditioning systems (fan coil units). UV lamps are positioned between photocatalyst-coated filter elements such that the filter elements serve as the photocatalytic surfaces. The filter geometry is stated to include honey-combs, fins, mesh, a filter-type structure, a fibrous type, or a filamentous structure.

U.S. Pat. No. 6,884,752 discloses an aqueous composition of titanium dioxide that includes varying amounts of acrylic aliphatic urethane polymer to improve wetability of the substrate, as well as, thinness and clarity of the produced film.

WO/2005/039659 discloses a germicidal air treatment method and device for air purification that consists of a longitudinal arrangement of UV light sources, inside an impermeable-walled enclosure, preceded by serial pre-filters (pre-filter, HEPA filter, and possibly a carbon filter), and equipped with a fan and motor. An ionizer is located downstream of the fan. UV irradiation is claimed for at least one side of one filter. The UV irradiation field within the UV treatment chamber is maximized by highly reflective walls (rough-surfaced aluminum, in the preferred embodiment). Components are arranged for turbulent air flow. This invention relies on filtration in place of photocatalysis, unlike the present invention.

U.S. Pat. No. 6,902,653 discloses fluid-permeable reticulated or packed bed photocatalytic reactors in which both the substrate and semiconductor photocatalyst are semi-transparent to the activating light. Fluid flow is either parallel or perpendicular to the lamp axis. The light sources are embedded within the packed bed.

U.S. Pat. No. 6,939,397 discloses a UV-based air-purifying apparatus of similar geometry to the present invention but involving an impermeable-walled, non-filtering, reflective-surfaced cartridge without any photocatalysis.

WO/2006/018949 discloses an air purifier and method for air purification that consists of a tubular (circular or polygonal section) main body having a plurality of air movement holes on the wall surrounding the inner space and an internal UV light source illuminating the inner wall surface. The formed, porous main body may be made of any photocatalyst-supporting fiber material, including cellulose and acrylic fibers. By forming projections and recesses on the inner surface, the irradiated surface area is increased. Air movement (in and out of the air movement holes), in the preferred embodiment, is provided (slowly) by convection resulting from lamp heat and diffusion. However, some forced air movement is suggested to be provided near the air movement holes by a discharge or intake fan. No filtration is claimed.

U.S. Pat. No. 7,063,820 discloses a method for disinfecting fluids on photocatalytic surfaces excited by UV-A irradiation within heating, ventilating, and air conditioning systems or in air ducts. An electrical bias applied to the photocatalytic elements is claimed to enhance the photocatalytic activity at low ambient humidity.

U.S. Pat. No. 7,083,659 discloses a combined light source and non-photocatalytic air purifier unit that has a cylindrical filter surrounding the fan. Therefore, the air flow through the filter is the reverse of the present invention and no photocatalysis is involved.

U.S. Pat. No. 7,144,840 discloses a method of preparation of small titanium dioxide crystals in a sol using polyethylene glycol as a dispersing agent before coating substrates and calcining the coated substrate.

U.S. Pat. No. 7,175,814 discloses an annular air disinfecting system and cartridge device containing ultraviolet light. While of similar annular geometry to the present invention, no photocatalysis is contemplated in this patent (only reflective surfaces). In this patent (unlike the present invention), the light source and other electronics are incorporated into the cartridge unit.

U.S. Pat. App. No. 2007084350 discloses a self-contained photocatalytic air purification apparatus comprised of a outer housing with air inlet and outlet ports enclosing sets of UV light sources illuminating both sides of one or more internal filters. Internal surfaces may be polished metal or coated with photocatalyst. Air flow is directed around a series of air baffles "to cause turbulence and to maximize exposure time." Exposure times are determined by air flow rates, not turbulence. Nevertheless, turbulence does improve the possibility of surface contact. In this invention, photocatalytic activity is limited by the smaller UV-illuminated photocatalyst-coated surface area and lesser intimate contact between airborne molecules and the smaller photocatalyst surface than in the present invention.

U.S. Pat. App. No. 20060086252 discloses a ceiling-mounted, single-sided, planar arrangement of UV lamps, photocatalytic filter, and active carbon coated filter in an air purifier. No detail is provided regarding the lamps or photocatalyst.

U.S. Pat. App. No. 20060086252 describes a photocatalytic air purifier comprised of a conventional lamp and shade arrangement in which the inner surface of the lamp shade is coated on the inner illuminated surface with a photocatalyst (broadly specified) such that heat generated by the light source (broadly specified) causes convection of air past the lamp shade surface. Convection alone is a slow process that generates a small number of air exchanges per hour in even modest sized indoor environments.

As noted above, organic binders for photocatalytic support structures are unsuitable as they emit unacceptable odors under UV-C irradiation. Further, Applicant has noted a heightened manufacturing cost associated with cylindrical support structures. Therefore there is a need for an improved and economical photocatalytic structure and apparatus implementing same.

SUMMARY OF THE INVENTION

In one embodiment of the invention, air purifying system is provided for conducting air along a sealed air flow path including through a photocatalytic element, a UV light source and a flow-inducing fan. The system comprises a two or more photocatalytic planar elements sealingly arranged to form a chamber or core cavity about the UV light source. The core cavity is sealed at one end and open to the fan at the other. Thus, the fan draws air along the sealed air flow path through the planer elements, into the core cavity and out of the core cavity adjacent the fan.

The planar elements and UV light source are located within a tubular housing supported on a base. The fan and controls are located in the base. In an embodiment, the tubular housing houses two or more photocatalytic planar elements sealingly arranged about the UV light source, forming a polygonal core cavity having a sealed periphery. A top end of the core cavity receives the UV light source and a top plate for sealing the top end. The core cavity is sealed at a bottom end to the base. A fan outlet is formed through the base and into the core cavity. The tubular housing is formed with air inlets for admitting air to the photocatalytic planar elements for treating air and the base has air outlets for discharging the treated air.

In an embodiment, each photocatalytic planar element comprises high-purity quartz fibers sandwiched between a screen secured into a frame. Thereafter the frame and quartz fibers are dipped into a solution containing a non-photocatalytically active material, such as peroxotitanic acid. The wet quartz fibers are dried and converted to anatase titanium dioxide ($TiO_2$). Each photocatalytic planar element can further comprise a pre-filter for intercepting air-borne particulates or contaminants before the air flow passes through the photocatalytic planar elements.

In another embodiment, an effective area of the photocatalytic elements, the UV light source and the arrangement of the elements to form the core cavity can be matched with the apparatus flow rate using methods set forth herein. The photocatalytic planar elements and light source are selected to provide the desired ultraviolet germicidal irradiation dosages (residence time inside the core cavity) at the prescribed air flow rates while maximizing the photocatalytic surface contact between the flowing air and the interiorly illuminated photocatalytically active medium. Turbulent flow also enhances air-surface contact.

An "average" ultraviolet germicidal irradiation dosage within the core cavity is estimated by first calculating a longitudinal "light-in-pipe" dosage and then dividing that result by about two, to account for an average transit time of a steady-state flow of air through the photocatalytic panels. This is about one-half the transit time of an equivalent flow of air entering in one end of the core cavity and exiting out the other. First a determination is made of the cumulative UV power density incident upon a surface K, being the cross-sectional area of the core cavity, oriented perpendicularly to the UV light source axis and located along the flow path in the core cavity, and then a calculation is made of the cumulative UV energy incident upon both sides of that surface K as it moves through the core cavity from one end to the other, at the same linear velocity as the air flow.

In a broad aspect of the invention, a system for purifying air by germicidal irradiation is disclosed. The system has air permeable elements, one embodiment of which is two or more planar elements sealingly arranged to form a polygonal shaped core cavity. A top end of the core cavity is sealed while a bottom end is open forming a sealed air flow path passing from an outside of the core cavity, through each of the planar elements, into the core cavity and exiting the core cavity at its open bottom end.

A source of UV radiation is disposed within the core cavity for irradiating air within the core cavity and an inside surface of each planar element. Some of the UV radiation contacting the inside surface is conducted and transmitted from the inside surface to an interior of each planar element for photocatalyzing germicidal irradiation of the air travelling through the interior.

Each planar element further comprises a photocatalytically active medium having a photocatalyst bound to a substrate that is conductive of and transparent to UV radiation.

In another broad aspect of the invention, a method of manufacturing a photocatalytic planar element for use in a germicidal irradiation system having at least three of the photocatalytic planar elements sealingly arranged to form a core cavity, sealed at a top end and open at a bottom end, for forming a sealed air flow path through the system is disclosed. The method includes the steps of providing a substrate that is conductive of and transparent to UV radiation; fitting the substrate in a planar frame; submerging the substrate and frame in a solution containing non-photocatalytically active material for wetting the panel therewith, for forming a non-photocatalytically active panel; and calcing the non-photocatalytically active panel for converting the non-photocatalytically active material to a photocatalyst bound to the substrate for forming the planar photocatalytically active element.

BRIEF DESCRIPTION OF THE DRAWINGS

The various features of the present invention may be more fully understood with reference to the following description and the accompanying drawings in which:

FIG. 9A is a perspective view of an embodiment of the present invention illustrating a frame for retaining a photocatalytic medium;

FIG. 9B is a perspective view of an embodiment of the present invention illustrating a screen for securing a photocatalytic medium within the frame of FIG. 9A;

DETAILED DESCRIPTION OF THE INVENTION

General Arrangement-Cylindrical Photocatalytic Element

Figure 1:
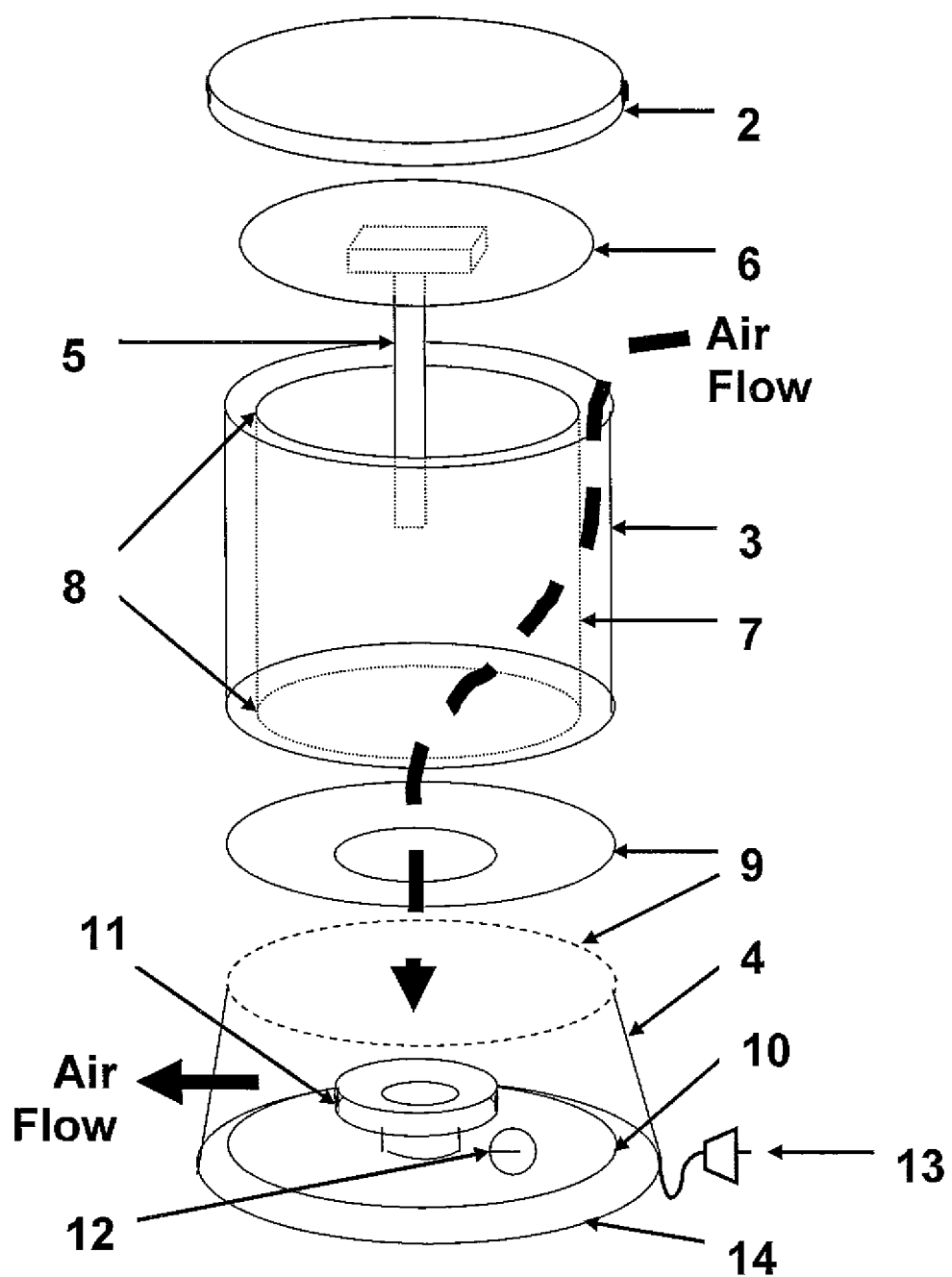
FIG. 1 is a schematic diagram indicating one embodiment of an assembled unit (including air flow) and the major component parts.

FIG. 1 is an illustrative schematic diagram of one embodiment of an air purifier system and unit according to the present invention. The system 1 generally includes the housing (top 2, sides 3, and base 4 with air exit ports or louvers), a photocatalyst-activating light source 5 and light source mounting plate 6, photocatalytic cartridge 7 with elastomeric gasket rings 8, photocatalytic cartridge end-seal plate 9 (with central port), electrical component mounting plate 10, fan and motor 11, speed control/switch 12, power cord 13, and base plate 14. When assembled, the mounting plate 6 and cartridge end-seal plate 9 form air-tight seals with the elastomeric gasket rings 8, shown as part of the photocatalytic cartridge 7.

Figure 2:
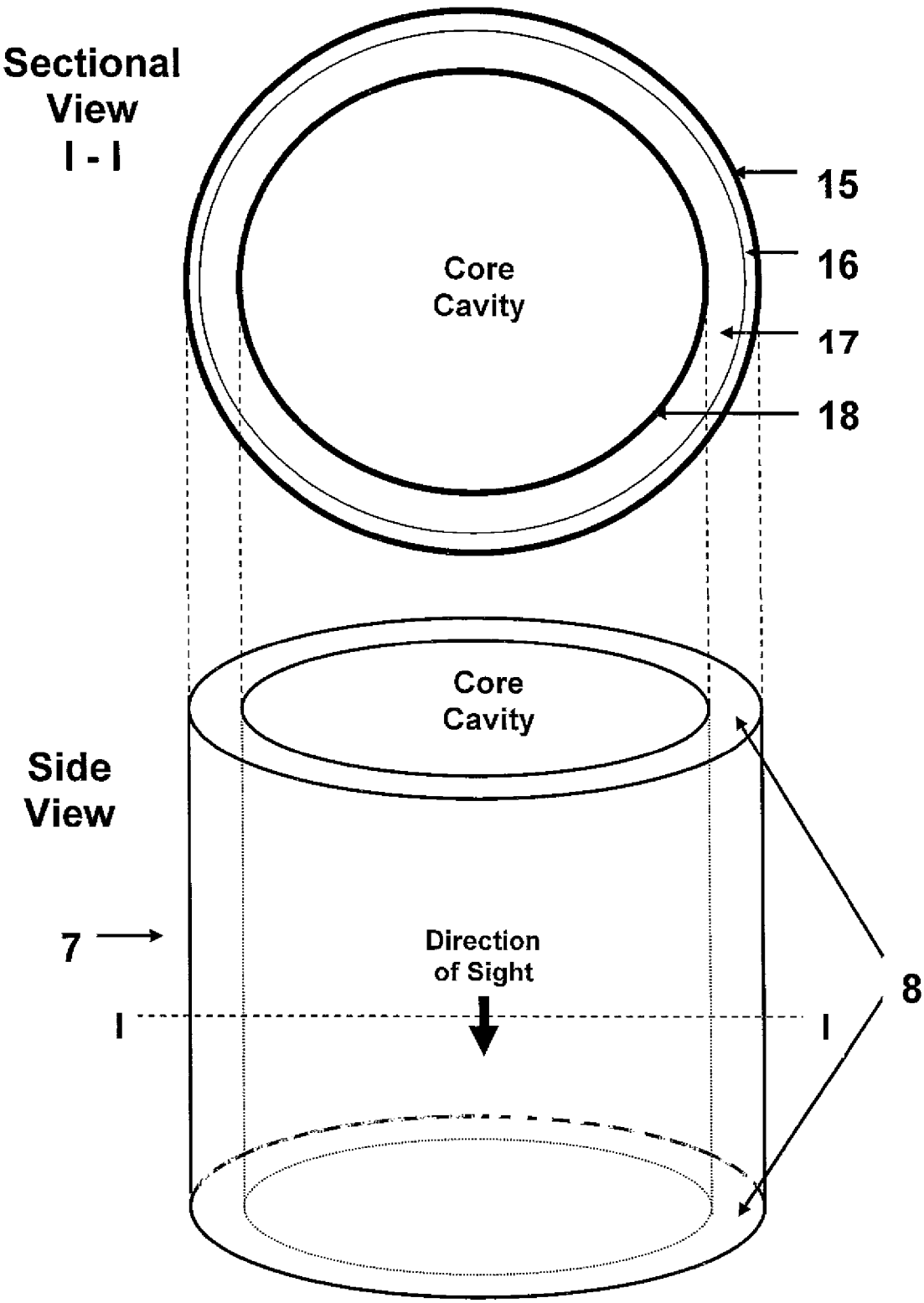
FIG. 2 is a schematic cross-sectional diagram showing the components of one embodiment of a photocatalytic cartridge.

FIG. 2 is a schematic diagram of components making up a preferred embodiment of the photocatalytic cartridge of claim 1. All elements are sealed inside the end enclosures (elastomeric rings 8, in a preferred embodiment) with an odor-free sealant 15. The outer mesh 15 (plastic or metal), in the preferred embodiment, serves only to physically protect the pre-filter medium 16 and the photocatalytic medium 17 and may provide little or no structural strength. Mesh "open areas" should be large enough so as not to restrict air flow. Concentrically inside or outside any protective mesh 15, is the pre-filter medium 16, pleated or un-pleated. A pleated pre-filter may be required (low air flow resistance) for very high air flow rates. However, un-pleated pre-filter media are adequate for most applications. The MERV rating of the pre-filter medium should be no less than 8 to keep clean the next-inside photocatalytic medium 17. In a preferred embodiment, the substrate material of the photocatalytic medium is a high-purity quartz fiber, wool, mat, or felt. However, a highly reflective metal wool, open-cell metal sponge, or open-cell metal foam, (e.g., of stainless steel or aluminum) could also be an effective substrate medium. The dominant photocatalytic substrate medium selection criterion is the survival of the UV light photons until absorbed by the photocatalytic coating. Non-conductive and non-reflective substrates do not permit penetration of the photons beyond the first encountered surface (any "shadowed" material is without photocatalytic effect). The finer are the fibers per gram, in the preferred quartz fiber embodiment, the larger is the substrate surface area available for photocatalysis. Ultra fine (2 micron diameter), fine (4 micron diameter), and coarse (9 micron average diameter) high-purity quartz fiber wool, mat, and felt materials are examples of such substrate media.

The innermost element of the photocatalytic cartridge is a rigid metal mesh 18 that provides the structural resistance to compression that permits formation of an air-tight seal between the plates 6 and 9 and the end ring closures 8 of the photocatalytic cartridge 7. In another embodiment, within the spirit of the present invention, the end ring closures 8 could be made of a non-gasket (non-elastomeric) material, with gaskets permanently fixed to the plates 6 and 9.

The biocidal performance of the present invention is the sum of two independent processes: (a) the ultraviolet germicidal irradiation, and (b) photocatalytic oxidation and reduction at or near the photocatalyst surface (the reaction zone). Photocatalysis alone is both germicidal and breaks down VCs into harmless reaction products, as understood and described in the prior art.

Ultraviolet Germicidal Irradiation

Figure 3:
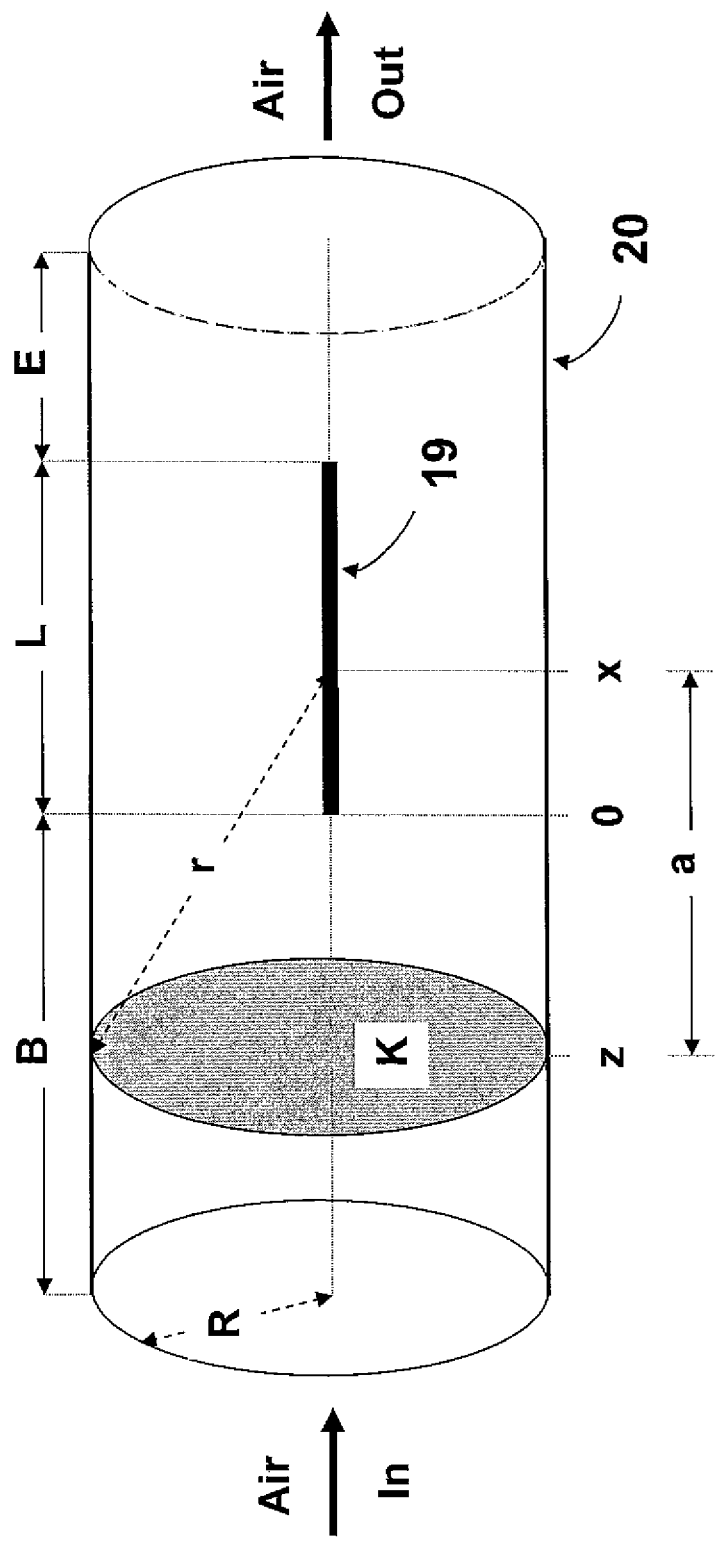
FIG. 3 is a schematic diagram illustrating "longitudinal light-in-pipe" parameters used to calculate the cumulative ultraviolet germicidal irradiation dosage in an air stream flowing through a cylinder/pipe parallel to a linear light source located on the cylinder/pipe axis.

To be germicidal, the wavelength of the radiation must be sufficiently short (energetic) to break chemical bonds or, at least, denature the DNA or proteins of microbes. This is generally accepted to be in the UV-C and UV-V ranges of the electromagnetic spectrum. The "average" ultraviolet germicidal irradiation dosage (energy per unit area irradiated) within the photocatalytic cylinder core cavity may be estimated by first calculating a longitudinal "light-in-pipe" dosage and then dividing that result by two to account for the fact that the average transit (residence) time of a steady-state flow of air, F (cubic feet per minute), entering through the permeable walls is one-half the transit/residence time of an equivalent flow of air entering in one end of the core cavity and exiting out the other. FIG. 3 is a schematic representation of a linear UV light source 19 (of length L) located on the center line (x-axis) of a cylinder 20 (of radius R and length B+L+E, open to air flow only at the ends). Determination of the UV dosages developed by the UV light source in this configuration involves two sets of calculations: (a) a determination of the cumulative UV power density (watt/cm$^2$) incident upon a surface K of area $\pi R^2$, oriented perpendicularly to the UV light source axis and located at any position "z" along the center line of the cylinder, and then (b) a calculation of the cumulative UV energy (watt-second/cm$^2$ or joules/cm$^2$) incident upon that surface K (both sides) as it moves through the cylinder from one end to the other, at the same linear velocity as the air flow.

If the inlet end of the light source is considered to be at the origin (zero) of the x-axis, then –B (negative B) is the x-coordinate of the inlet end of the cylinder, L is the x-coordinate of the outlet end of the light source, and L+E defines the x-coordinate of the outlet end of the cylinder 20.

UV Power Density

If the UV output of the light source is W watts, evenly distributed along its length, L, then each infinitesimal element, dx, of the UV source at a position "x" along its length may be considered as a "point source" of UV light, radiating uniformly in all directions. The infinitesimal UV output, dW, attributable to this element, dx, is:

$$dW = (W/L)dx$$

If the surface K is located at position "z", a distance "a" to the left of "x", the total sphere area, S, of radius "r" surrounding the point at "x" is $$S = 4\pi r^2, \text{ and}$$

the area of the "slice" of that sphere with base K defined by the solid angle subtended by K at x is $$A = 2\pi r(r-a),$$

such that the fraction of the total irradiance from dW at x, falling on K is $$A/S = (r-a)/2r$$
$$= 0.5 * (1 - a/r).$$

But $a = x - z$ and $r^2 = a^2 + R^2$, so that
$$A/S = 0.5 * \{1 - (x-z)/[(x-z)^2 + R^2]^{1/2}\},$$

and the average power density, $dI_z$, incident upon K from dW at x is $$dI_z = (A/S) dW/K \text{ watts/cm}^2$$

Integrating over all infinitesimal elements $dI_z$ of the UV light source (from x=0 to x=L), yields the average power density (watts/cm$^2$) received by surface K at position "z".

$$I_z = \int dI_z$$
$$= (W/(K*L)) \int (A/S) dx, \text{ integrating over the whole bulb length}$$
$$(x = 0 \text{ to } L).$$
$$= (W/(2*K*L)) * \{L - [(L-z)^2 + R^2]^{1/2} - [z^2 + R^2]^{1/2}\}$$

UV Energy Dosage

If the steady-state air flow rate is F (cubic feet per minute or "cfm"), the average linear velocity of the air and K is F/K (feet per minute, where K is measured in square feet). Therefore, the transit time for air to traverse the cylinder/pipe, i.e., K to travel from –B to L+E along the x-axis is (B+L+E)*K/F. Therefore, the cumulative UV dosage (watt-sec./cm$^2$ or joule/cm$^2$), CD, delivered by the UV light source and received by area K traversing the cylinder/pipe is the sum of three parts: the two single-sided end contributions, $CD_B$ and $CD_E$, and the two-sided (both sides of K) contribution at the bulb, $CD_L$.

$$CD = CD_B + CD_L + CD_E \qquad \text{EQUATION 1}$$
$$= \int I_z dt,$$

integrating between
$$t = -BK/F(z=-B) \text{ and } t=(L+E)*K/F(z=L+E).$$

But the steady-state linear velocity F/K=dz/dt=dx/dt, so that dt=(K/F)dz, and so $$CD_B = (K/F) \int I_z dz, \text{ integrating between } z = -B \text{ and } z = 0$$
$$= (W/(2*F*L)) * \{B*L + 0.5*(B*[B^2 + R^2]^{1/2} +$$
$$L*[L^2 + R^2]^{1/2} - (L+B)*[(L+B)^2 + R^2]^{1/2} +$$
$$R^2 \ln\{(R*(L + (L^2 + R^2)^{1/2}) / (([B^2 + R^2]^{1/2} - B)*$$
$$(L + B + [(L + B[(L+B)^2 + R^2]^{1/2})))\})$$

$$CD_L = 2(K/F) \int I_z dz, \text{ integrating between } z = 0 \text{ and } z = L$$
(both sides of K)
$$= W*L/F$$

$$CD_E = (K/F) \int I_z dz, \text{ integrating between } z = L \text{ and } z = L + E$$
$$= (W/(2*F*L)) * \{E*L + 0.5*(E*[E^2 + R^2]^{1/2} +$$
$$L*[L^2 + R^2]^{1/2} - (L+E)*[(L+E)^2 + R^2]^{1/2} +$$
$$R^2 * \ln\{(R*(L + (L^2 + R^2)^{1/2}) / (([E^2 + R^2]^{1/2} - E)*$$
$$(L + E + [(L + E + [(L+E)^2 + R^2]^{1/2})))\})$$

These formulae assume no internal reflection of any photons. For a "permeable-walled" photocatalytic (PC) cartridge, the cumulative UV dosage is one-half the calculated CD. In this dynamical system, only the end dosages ($CD_B$ and $CD_E$) formulae involve R, and each are of the same form. Within the length of the bulb (z=0 to z=L), the dosage, $CD_L$, involves only W, L, and F, with no explicit dependence upon K (integrals involving R cancel). While this result is somewhat counter-intuitive, it can be understood by the linear velocity of K as F/K, such that, for example, when K is doubled, the linear velocity of K is halved so the dosage remains the same. When B and E are zero, $CD_B$ and $CD_E$ are also zero, respectively.

TABLE 1

Illustrative Cumulative UVGI Dosage (CD) Formula Results*

| UV-C Bulb Rating (Watts): | 18 W | | 36 W | | 36 W | |
|---|---|---|---|---|---|---|
| Number of Bulbs: | 2 | | 1 | | 2 | |
| UV-C Output: % | 30.8% | | 30.8% | | 308% | |
| UV-C Watts, W | 11.1 | | 11.1 | | 22.2 | |
| Envelope Length, L (Inches): | 7.5 | | 15.0 | | 15.0 | |
| Cartridge/Pipe Parameters: | | | | | | |
| Length, B + L + E (Inches): | 10.0 | | 10.0 | | 10.0 | |
| Distance before Bulb, B (Inches): | 1.5 | | 1.5 | | 1.5 | |
| Distance after Bulb, E (Inches): | 1.5 | | 1.5 | | 1.5 | |
| Internal Radius, R (Inches): | 4.0 | | 4.0 | | 4.0 | |
| Air Flow, F (cfm):* | 50 | 100 | 50 | 100 | 50 | 100 |
| UVGI Dosage, CD (µwatt-sec/cm²): | | | | | | |
| $CD_B + CD_E$ | 499 | 250 | 292 | 146 | 584 | 292 |
| $CD_L$ | 8,951 | 4,475 | 17,903 | 8,951 | 35,805 | 17,903 |
| Impermeable Pipe ($CD_B + CD_E + CD_L$): | 9,450 | 4,725 | 18,194 | 9,097 | 36,389 | 18,194 |
| PC Cartridge (permeable walls): | 4,725 | 2,362 | 9,097 | 4,548 | 18,194 | 9,097 |

*Note:
for a room volume of 1,000 cubic feet, an air flow of 50 cfm provides 3 air exchanges per hour and 100 cfm provides 6 air exchanges per hour.

The results in TABLE 1 are self-consistent to the extent that doubling the air flow rate halves the UV dosage and halving the UV output (one 36 W bulb in place of two) also halves the UV dosage. Furthermore, a longer UV bulb extends the residency time in the radiation field of the UV light source and, hence, the greater UV dosage calculated for one long 36 W bulb versus two short 18 W bulbs. These results also imply consistent units conversions (imperial units to metric units and vice versa). The dosage units are W-sec/cm² (or J/cm²), which must be multiplied by 1,000,000 to convert to the usual units µW-sec/cm² or µJ/cm² as commonly used in the literature. Ninety percent (90% or "one log") of many airborne species of molds, bacteria, and viruses are killed or "deactivated" at dosages well under 10,000 µW-sec/cm² (or 100 J/m², see References 1-4).

Photocatalytic Substrate Fiber Area and Coating Density

High purity quartz has a density of 2.20 g/cm³. Therefore, a given weight (grams), W, of quartz fiber material has a volume, V, where $$V = L \times \pi R^2, \text{ where } L \text{ is the total fiber length (cm) and}$$

$$R \text{ is the average fiber cross-sectional radius (cm)}$$

$$= W / 2.20 \text{ cm}^3, \text{ and}$$

$$L = W / (2.20 * \pi R^2) \text{ cm}$$

The photocatalyst-coatable fiber surface area, A, is then given by the fiber circumference times the length, L:

$$A = 2\pi R \times L \text{ cm}^2 \quad\quad\quad \text{EQUATION 2}$$

$$= 4W / (2.20 * D) \text{ cm}^2,$$

where $D = 2R$ is the fiber diameter in cm.

For a coarse quartz wool (9 micron=9×10⁻⁴ cm diameter fibers), each gram of such wool presents a total coatable fiber surface area of $4/(2.20*9\times10^{-4})$ or $2.02\times10^3$ cm².

Figure 4:
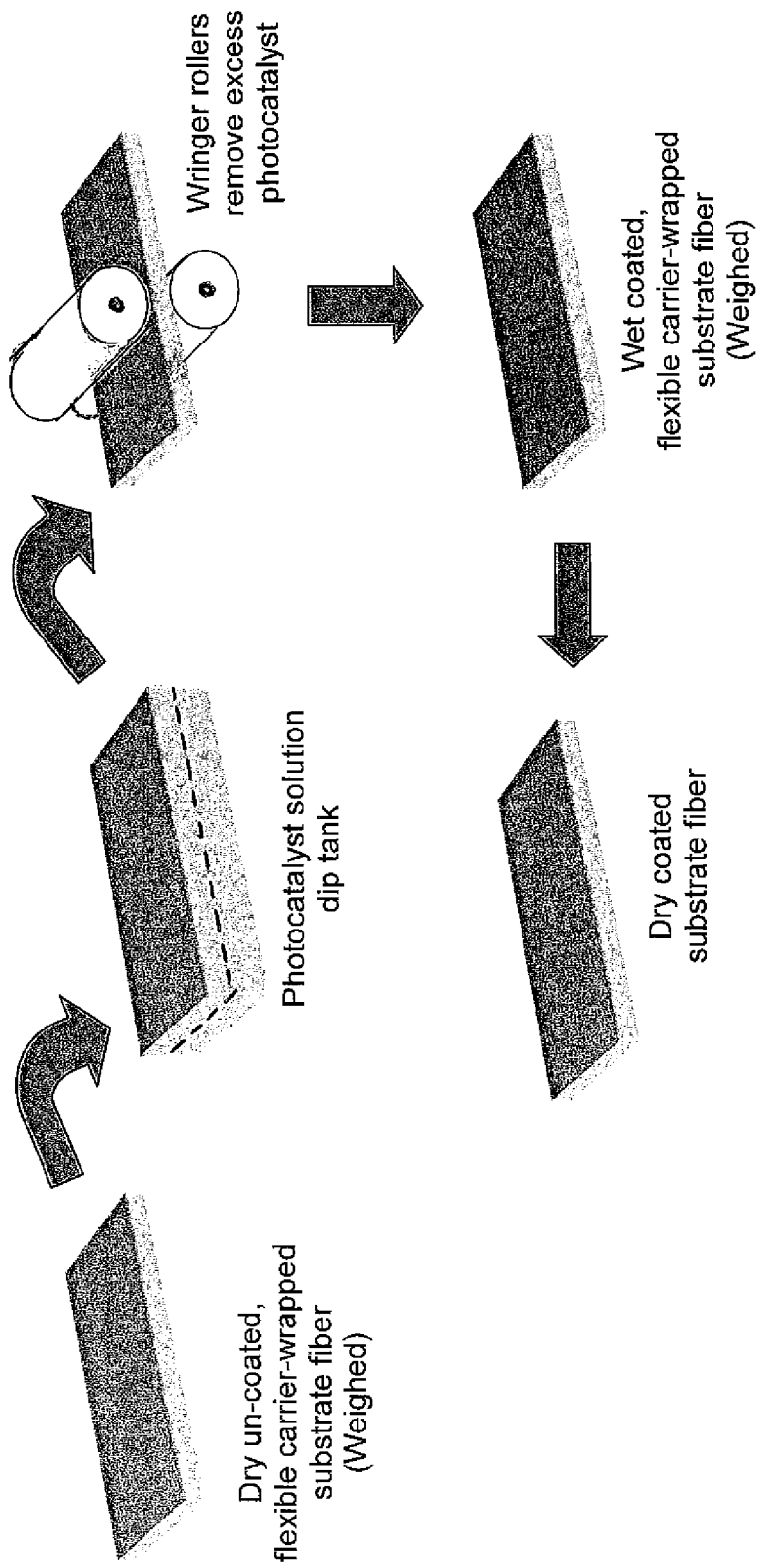
FIG. 4 is a schematic diagram illustrating the coating process of a quartz fiber photocatalyst substrate, according to one embodiment of the present invention.

FIG. 4 provides a schematic representation of a dip-coating process for coating a known weight, $S_D$, of dry photocatalytic substrate fiber material (wool, mat, or felt) with a determinable surface coating of photocatalyst starting with a sol gel solution of known concentration, C (e.g., g/ml of anatase $TiO_2$). Given the density, ρ, of the sol gel solution and the weight of the sol-gel wet substrate fiber mass, $S_W$, the weight of retained dry photocatalyst coating, PC, may be calculated as PC=$(S_W-S_D)$*C/ρ grams, such that the coating density on the fiber surface is:

$$\text{Coating Density}=PC/A \quad\quad\quad \text{EQUATION 3}$$

Figure 5:
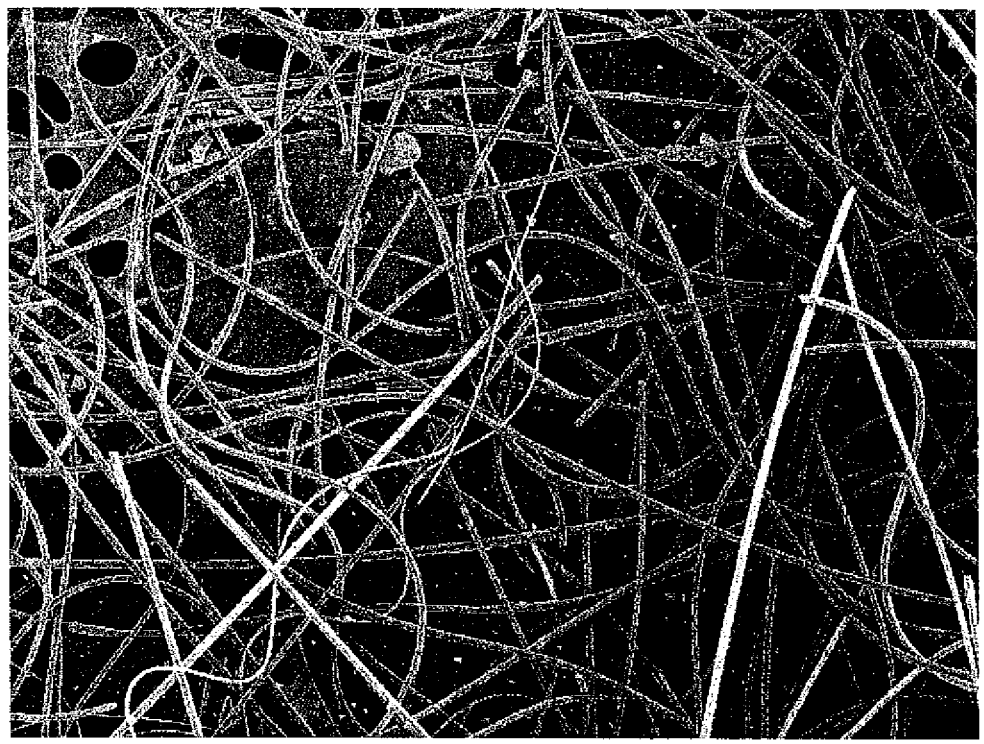
FIG. 5(a) is a scanning electron micrograph (SEM) of photocatalyst-coated 9 micron diameter (average) quartz fibers at 100× magnification.
FIG. 5(b) is an SEM of the same photocatalyst-coated 9 micron diameter (average) quartz fiber sample at 500× magnification.
Figure 5:
Figure 6:
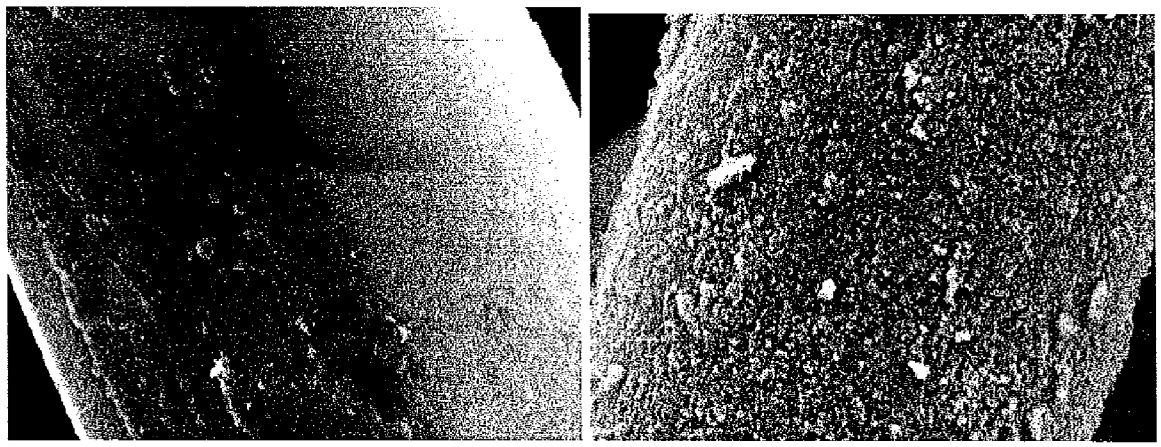
FIG. 6(a) is an SEM of a single un-coated quartz fiber at 15,000× magnification.
FIG. 6(b) is an SEM of a single photocatalyst-coated quartz fiber at 15,000× magnification.
FIG. 6(c) is an SEM of a single un-coated quartz fiber at 70,000× magnification (near the limit of clear resolution).
FIG. 6(d) is an SEM of the broken end of a coated quartz fiber, at 15,000× magnification, to show that the coating thickness is a very small fraction of the fiber diameter.
Figure 6:
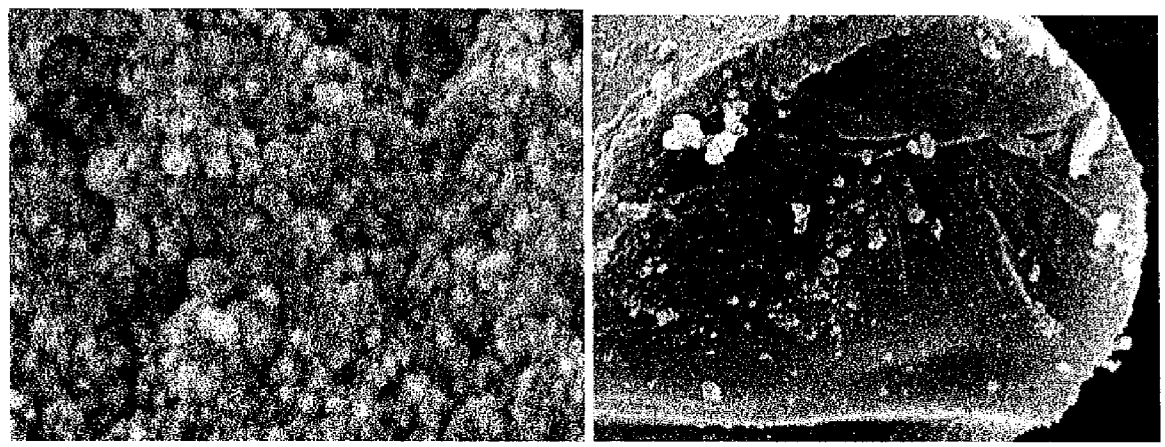

FIG. 5(a) and (b) are scanning electron micrographs of a "nominal" (average) 9 micron diameter photocatalyst-coated quartz wool at 100× and 500× magnifications, respectively. The diversity of fiber diameters and the bends and the breaks in the fibers are evident in these images. Increasing the magnification to 15,000× of one of the un-coated and coated fibers in FIG. 6(a) and FIG. 6(b), respectively, shows the excellent coverage but very "rough" surface of the dried photocatalytic coating (FIG. 6(b)). A further magnification to 70,000× in FIG. 6(c) shows visible "agglomeration" of particles in the 10 to 100 nm range.

Figure 7:
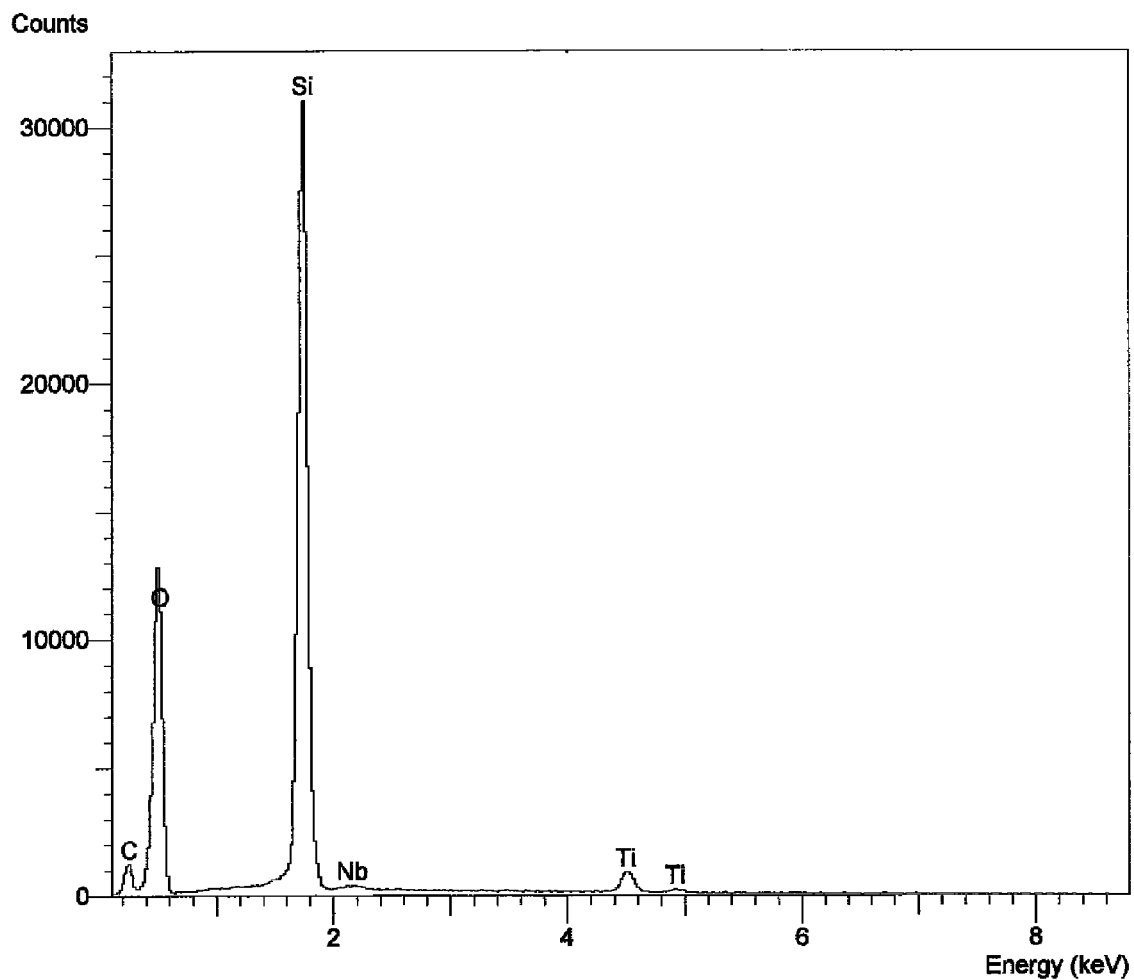
FIG. 7 is an energy-dispersive x-ray spectroscopy (EDS) spectrum (elemental analysis), of the coated fibers.

Elemental analysis, using energy-dispersive x-ray spectroscopy (EDS), of the coated fibers is shown in FIG. 7. This analysis shows the expected silicon dioxide and titanium dioxide with "trace" amounts of un-expected carbon and niobium probably due to the sample retaining tape and possibly also due to the sample holder for the analysis.

Photocatalyst Coating Thickness and Area

A photocatalytic cartridge containing 40 g of nominal 9 micron quartz fiber adsorbed 109.1 ml of 2.20% titanium dioxide sol gel also containing peroxotitanic acid binder with a combined solution density of 1.032 g/ml (0.0227 g/ml anatase sol gel and 0.0103 g/ml peroxotitanic acid binder). The retained sol gel weight implies 2.477 g of $TiO_2$ (formula weight of 79.87 amu) or $3.101\times10^{-2}$ mols. By EQUATION 2, this weight of quartz wool has an estimated surface area of $4*40/(2.20*9)\times10^6$ cm² or $8.081\times10^6$ cm². Therefore, the formula weight units (mols) per cm² are $3.101\times10^{-2}/8.081\times10^6=3.837\times10^{-9}$ mols/cm². The unit cell dimensions of nanocrystalline anatase (see Weirich, Reference 5) are 3.872× 3.872×9.616 cubic angstroms=0.14417 cubic nm or 0.03604 nm³ per $TiO_2$ unit (four $TiO_2$ units per anatase unit cell). Therefore, a densely packed "spherical" 10 nm diameter particle would contain approximately 14,528 $TiO_2$ formula units. Furthermore, given the Avogadro Number of formula units per mol (i.e., $6.022045 \times 10^{23}$), the number of mols/cm$^2$ implies $3.837 \times 10^{-9} \times 6.022045 \times 10^{23}/14,528 = 1.590 \times 10^{10}$ of 10 nm particles/cm$^2$. Assuming hexagonal closest packing of spheres, a single layer of 10 nm particles would have an areal packing density of approximately $12 \times 0.5 \times 5 \times 10$ nm$^2$=300 nm$^2$ per 3 particles or 100 nm$^2$ per each 10 nm diameter particle. Each square cm of substrate fiber surface would then accommodate $1/(100 \times 10^{-14}$ cm$^2$ per particle) particles in a single layer or $1 \times 10^{12}$ particles per cm$^2$ of substrate surface. This is more than the above calculated $1.590 \times 10^{10}$ particles/cm$^2$ applied. This result implies a surface coating with gaps between 10 nm particles or an average "mono-layer" particle size of less than 10 nm diameter, i.e., about 1 nm diameter with about 7 formula units per particle. The greater apparent coverage than calculated for surface density of "compact" 10 nm particles suggests that the agglomerations of FIG. 6(c) are not compact, but loosely packed (possibly porous) and of low volumetric density.

A mono-layer of three-dimensional close-packed spheres (of uniform diameter) on a two-dimensional planar surface have a total sphere surface area to plane surface area ratio of $2\pi/\sqrt{3} = 2.094$, independent of sphere diameter. Therefore, an estimate of photocatalyst area on a uniformly covered (no gaps) substrate surface is 2.094 times the substrate surface area. In the example of 9 micron diameter coarse quartz wool (see above), this implies a photocatalyst surface area of approximately $2.094 \times 2.02 \times 10^3$ cm$^2$ per gram of photocatalyst, further enhanced by the distribution of photocatalyst particle sizes and surface roughness. While not all of this photocatalyst surface is accessible to UV photons, errors of over-estimation and under-estimation are expected to approximately cancel each other.

FIG. 6(d) shows a SEM of a cross-section (broken end) of a coated quartz fiber at 15,000× magnification. One millimeter, on the scale of this figure, translates to approximately 100 nm. Therefore, the thickness of the "loosely packed" coating (barely visible at the right-hand edge of the fiber) is estimated to be less than 100 nm. However, silica dust particles on the fibers, prior to coating, further add to (enhance) the coated fiber surface "roughness" and the photocatalytically active surface area.

Fiber Geometry and Orientation

As discussed by Peill, et al., in U.S. Pat. Nos. 5,875,384 and 6,051,194, as fiber thickness is increased, photons undergo fewer reflections at the quartz-TiO$_2$ interface for a fixed incident angle and a given length, such that with a thicker diameter fiber, the probability that a photon will be refracted through the quartz-TiO$_2$ interface is reduced. The small diameter fibers and tangled (many bends) nature of the quartz wool of this invention (as shown in FIG. 5(a) and FIG. 5(b)) ensures a higher probability that a photon will be refracted through the quartz-TiO$_2$ interface and absorbed by the coating. While Peill, et al., in U.S. Pat. Nos. 5,875,384 and 6,051,194 concluded that chemical efficiency would be enhanced by employing larger diameter fibers in their fiber cable reactor, the opposite is true of this invention.

Light Intensity and Wavelength Dependence

To be germicidal (without photocatalysis), the UV irradiation should be in the more energetic UV-C to UV-V ranges. As noted in prior art, photocatalytic activity also occurs with less energetic UV-A and UV-B irradiation. Irradiation saturation effects were noted by Peill, et al., in U.S. Pat. Nos. 5,875,384 and 6,051,194, where a four-fold increase in the quantum efficiency (of photo-oxidation/reduction reactions) was achieved with a two-order of magnitude reduction in the absorbed light intensity. However, optimization was stated to be achieved by increasing the fiber number density, which would divide the photon flux among more fibers and thus present a greater photocatalytic area (as achieved by the present invention).

In summary, embodiments of the photocatalytic air purifier system comprise an outer housing, an ultraviolet or near ultraviolet (UV, 100 to 450 nm wavelength range) light source (photocatalyst-activating), air inlet port(s) and air outlet port(s), a variable speed fan and motor, and a cylindrical, replaceable, photocatalytic cartridge located concentrically about the longitudinal axis of the UV light source and closed to air flow at one end, such that air flow is directed inward through the photocatalytic cartridge walls and out the open end. The source of photocatalyst-activating UV radiation or light source can be any UV generating lamp or columnar array of light emitting diodes (LEDs).

The UV source can be mounted to a mounting plate. The mounting plate can further be used to seal an upper end of the cartridge to force air through the core cavity, illuminated with UV radiation, and out an open lower end which abuts against a centrally ported plate. The mounting plate can be sealed against the upper end of the cartridge with any sealing means, such as a ring gasket. The lower end of the cartridge can also be sealed by any sealing means, such as a second ring gasket.

In another embodiment, the photocatalytic cartridge comprises a photocatalytic medium, such as a permeable material coated with a photocatalyst. An example of a photocatalytic coating can be a microcrystalline anatase titanium dioxide-based coating bound to the surface of the medium with a UV-resistant inorganic binder. The inorganic binder can be, for example, peroxotitanic acid or a derivative thereof. The thickness of the photocatalytic medium should be of sufficient thickness to provide for complete or near complete extinction of the UV light at an outside surface adjacent the pre-filter medium for preventing deterioration of the pre-filter medium. As known in the art, organic binders will deteriorate upon exposure to UV radiation.

The photocatalytic medium substrate can be a high-purity, UV-transparent quartz fiber material, such that all surfaces of the medium are fiber-optically or reflectively accessible by the UV light to maximize the photocatalytic efficiency of the UV radiation. The photocatalytic medium substrate can be a loosely tangled or random oriented fibrous wool, mat, or felt that allows turbulent air flow on passage through the medium and multiple particle/molecular contacts at or near the photocatalytic surface (the reaction zone).

The method of coating the photocatalytic substrate medium with the photocatalyst is effected by wrapping a weighed quantity of the substrate medium in a flexible carrier mesh that remains strong when wet, such as a fiberglass mesh fabric. The wrapped substrate medium is then immersed, submerged or dipped in a photocatalyst sol solution. In an embodiment, a surfactant can be added to the photocatalyst sol solution to ensure good coverage of the quartz fibers. Excess photocatalyst sol solution can be removed by wringing out the excess solution, from the saturated substrate medium in the carrier mesh, between soft rubber rollers. The saturated substrate medium is weighed to measure sol retention (coverage), and then set aside to dry or bake. The dried substrate medium can now be incorporated into the cartridge.

The method of construction of the photocatalytic cartridge and coating technique avoids de-lamination of the photocatalyst coating from the substrate medium under normal air purification operating conditions.

The use of high-purity quartz fibers of known average fiber diameter and weight, as a substrate material, permits a calculated estimate of the effective (UV light accessible) surface area of the substrate fiber available for photocatalysis.

EQUATION 1 can be used to calculate the average ultraviolet germicidal irradiation dosage delivered by the UV light source within the illuminated core cavity of the photocatalytic cartridge. EQUATION 2 can be used to calculate the available fibrous substrate surface area of the quartz fibers used. EQUATION 3 can be used to calculate the photocatalyst coating coverage density of the fibrous substrate within the photocatalytic cartridge.

Further, the coaxial geometry of the cylindrical cartridge allows for easy scaling of unit dimensions to accommodate a wide range of UV light sources, UV power ranges, photocatalysts, substrate media, air flow rates, and noise level requirements. The air inlet port area, annular area (between the outside of the cartridge and outer housing wall), the fan and fan-outlet port areas can be adapted so as not to restrict air flow and to minimize and dampen "air rush" noise.

In another embodiment, the photocatalytic cartridge can further comprise a metal or plastic protective mesh and a layer of pleated or unpleated pre-filter material. In a preferred embodiment, the pre-filter is un-pleated with no less than a MERV 8 rating. The pre-filter positioned at an outside wall surface of the photocatalytic cartridge removes particulates from the air and keeps the UV irradiated quartz fiber surfaces free of particulates to increase the economic life of the cartridge (i.e., until air flow resistance created by pre-filter plugging becomes excessive). The pre-filter can further enclose a layer of photocatalytic medium wrapped about an inner, structurally rigid, metal mesh. The pre-filter can also be sealed by elastomeric gasket rings at an upper end and a lower end, such that only the cartridge core cavity is open at both ends.

Photocatalytic Planar Elements and Methods of Manufacture

As described above, in contradistinction to the prior art, Applicant's fibrous UV-conducting substrate for the photocatalyst has small diameter fibers and are in a random, tangled or non-oriented arrangement for providing many bends, increasing the probability of a photon being refracted through the substrate-photocatalyst coating interface and be absorbed by the coating. Further manufacturing advantage is gained in the structure into which the substrate and photocatalyst are arranged.

A cylindrical photocatalytic cartridge as taught in the above embodiment can pose challenges in manufacturing, as the photocatalytically active medium must be formed in a cylindrical shape. Some economy in manufacturing can be achieved by using alternative photocatalytic planar elements as disclosed herein below. The planar elements themselves introduce separate challenges involving the incorporation of the planar elements into an integrated system and manufacture of the elements.

Two or more air permeable photocatalytic planar elements, in conjunction with spacing structures, can be sealingly arranged to form a polygon (replacing the cylindrical photocatalytic cartridge 7 above) defining a polygonal shaped core cavity. A top end of the core cavity is sealed, while a bottom end of the core cavity remains open. The sealing arrangement of the core cavity creates a sealed flow path for the air, ensuring that air will travel from a surrounding environment, through the planar elements, into the core cavity and out through the open bottom end.

A source of UV radiation is disposed within the core cavity to irradiate air within the core cavity and also an inside surface of each planar element facing the UV source. The UV radiation can also be conducted or transmitted to an interior of the planar elements to irradiate the air travelling within the planar elements.

Air travelling along the sealed flow path, through the planar elements and through the core cavity, is purified and then expelled through the open bottom end of the core cavity, to be released or returned to the surrounding environment.

Figure 8:
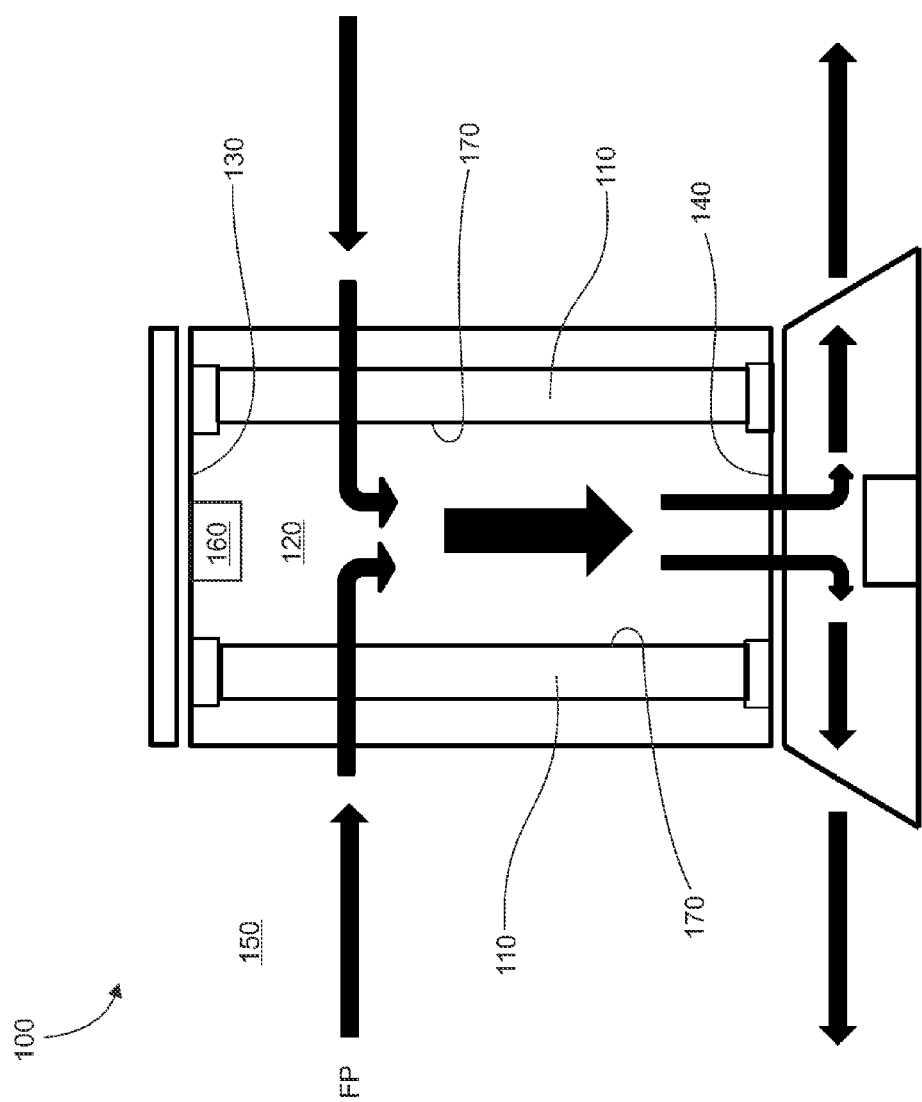
FIG. 8 is a perspective view of an embodiment of the present invention, illustrating photocatalytic planar elements sealingly forming a polygonal shaped core cavity.

As shown in FIG. 8, the air purifier system 100 can comprise three or more air permeable planar elements 110 sealingly arranged to form a polygonal shaped core cavity 120. The core cavity 120 has a sealed top end 130 and an open bottom end 140, ensuring that air will flow in a sealed air flow path FP passing from an outside of the core cavity 150, through the planar elements 110, into the core cavity 120 and to exit the core cavity 120 through the open bottom 140.

The planar elements 110 can be arranged to form a polygon defining a polygonal shaped core cavity 120, which would replace the cylindrical photocatalytic cartridge 7 of the previous embodiment. A skilled person would understand that the three or more planar elements (triangular cross-section) can be 4, 5, 6 or more planar elements sealingly arranged to form or define the polygonal shaped core cavity, such as a square, pentagonal, hexagonal cross-sections respectively.

A UV radiation source 160 is placed within the core cavity 120 for irradiating air within the core cavity 120 as well as an inside surface 170 of each planar element 110.

Each planar element 110 further comprises a photocatalytically active medium. The medium can be a substrate that is conductive of and transparent to UV radiation, having a photocatalyst coating bound thereto. As the UV radiation source irradiates the inside surface 170 of each planar element 110, some of the UV radiation is conducted and transmitted from the inside surface 170 to an interior of each planar element 110 for promoting photocatalytic reactions in the air travelling through the interior. Conduction of and transmission of some of the UV radiation can be through both refraction and reflection of UV radiation by the substrate. The substrate is of sufficient purity, such as high-purity quartz, so as to conduct UV photons to the interior of the element 110. UV radiation transmitted into the interior of each planar element 110 continues to be transmitted until such time as being absorbed by the photocatalyst.

As described above, EQUATION 1 can be used to calculate the average ultraviolet germicidal irradiation dosage delivered by the UV light source within the illuminated, cylindrical, core cavity of the photocatalytic element. A person skilled in the art would understand that comparable results for other geometries of the core cavity can be calculated by applying the ratio of cross sectional areas of whatever polygonal shape the cartridge may be (ie. square, hexagonal, octagonal).

Figure 9C:
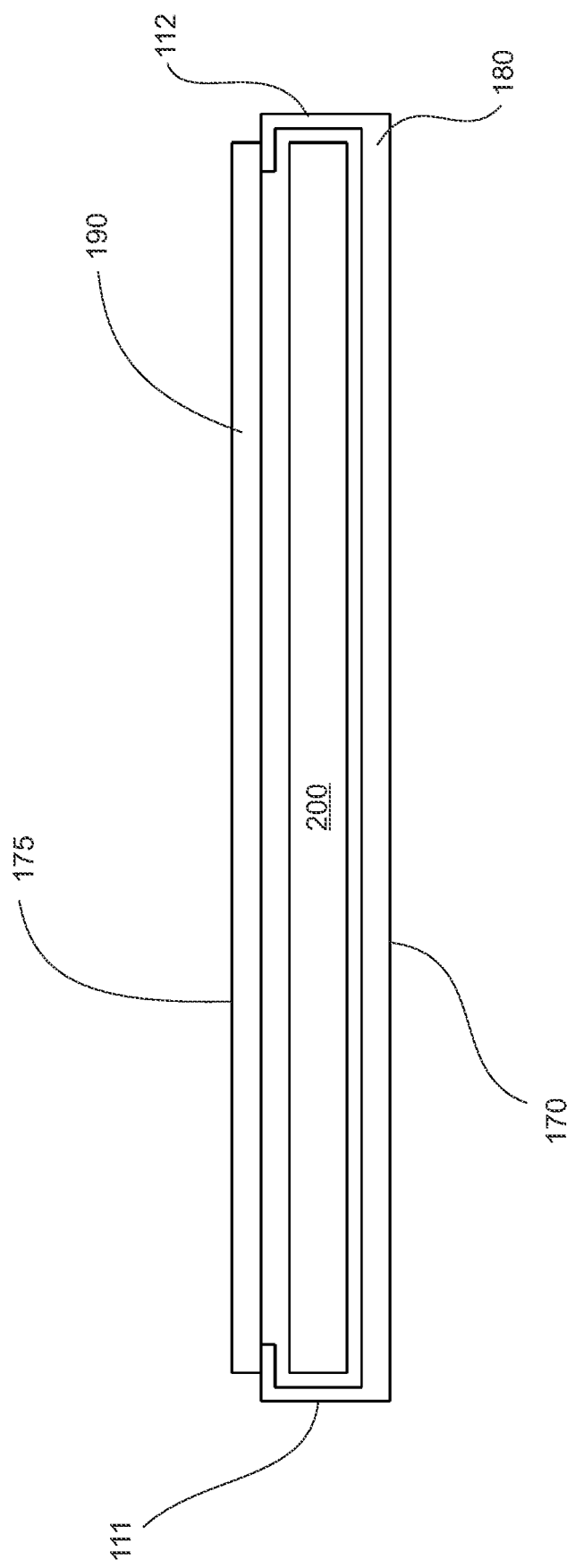
FIG. 9C is a schematic side view of a non-photocatalytically active panel, having a substrate fit secured within the frame of FIG. 9A by the screen of FIG. 9B.

With reference to FIGS. 9A to 9C, each planar element 110 can comprise a photocatalytically active medium 200 secured within a frame 180 by a screen 190. The photocatalytically active medium 200 can comprise a substrate coated with a photocatalytic material, such as a photocatalyst bound to the substrate. The substrate can be a fibrous substrate, such as high-purity quartz fibers, in a loose, random or non-oriented containment. The high-purity quartz fibers are conductive of and transparent to UV radiation for maximizing the transmission of UV radiation into the interior of the planar element 110. An example of high-purity quartz fibers is QUARTZEL® which is commercially available as a quartz wool mat stored as large rolls and available from Saint Gobain (www.quartz.saint-gobain.com/quartzel.aspx).

In addition to the light conductance capabilities, the non-oriented containment of the quartz fibers also provide a large surface area available for the photocatalyst. Furthermore, non-oriented containment provides a low air flow resistance while ensuring that the air flow is turbulent and evenly distributed within the interior of the planar elements. Turbulent air flow increases a residence time for air travelling through the interior, allowing more time for the air to be exposed to the germicidal effects of photocatalytic irradiation.

Figure 10A:
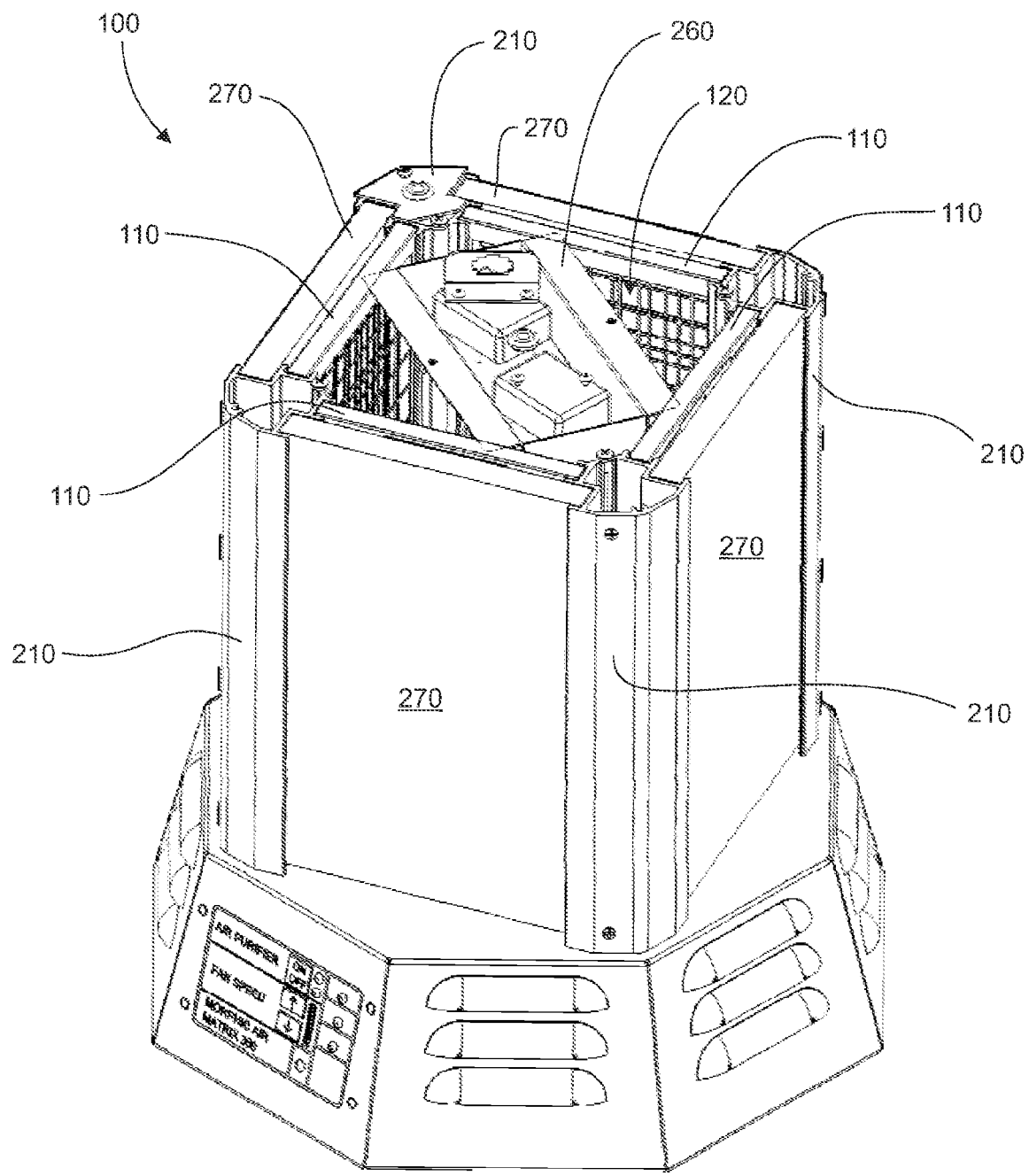
FIG. 10A is a perspective view of an embodiment of the present invention illustrating four photocatalytic planar elements sealingly arranged to form a rectangular core cavity having a UV source disposed within the core cavity.
Figure 10B:
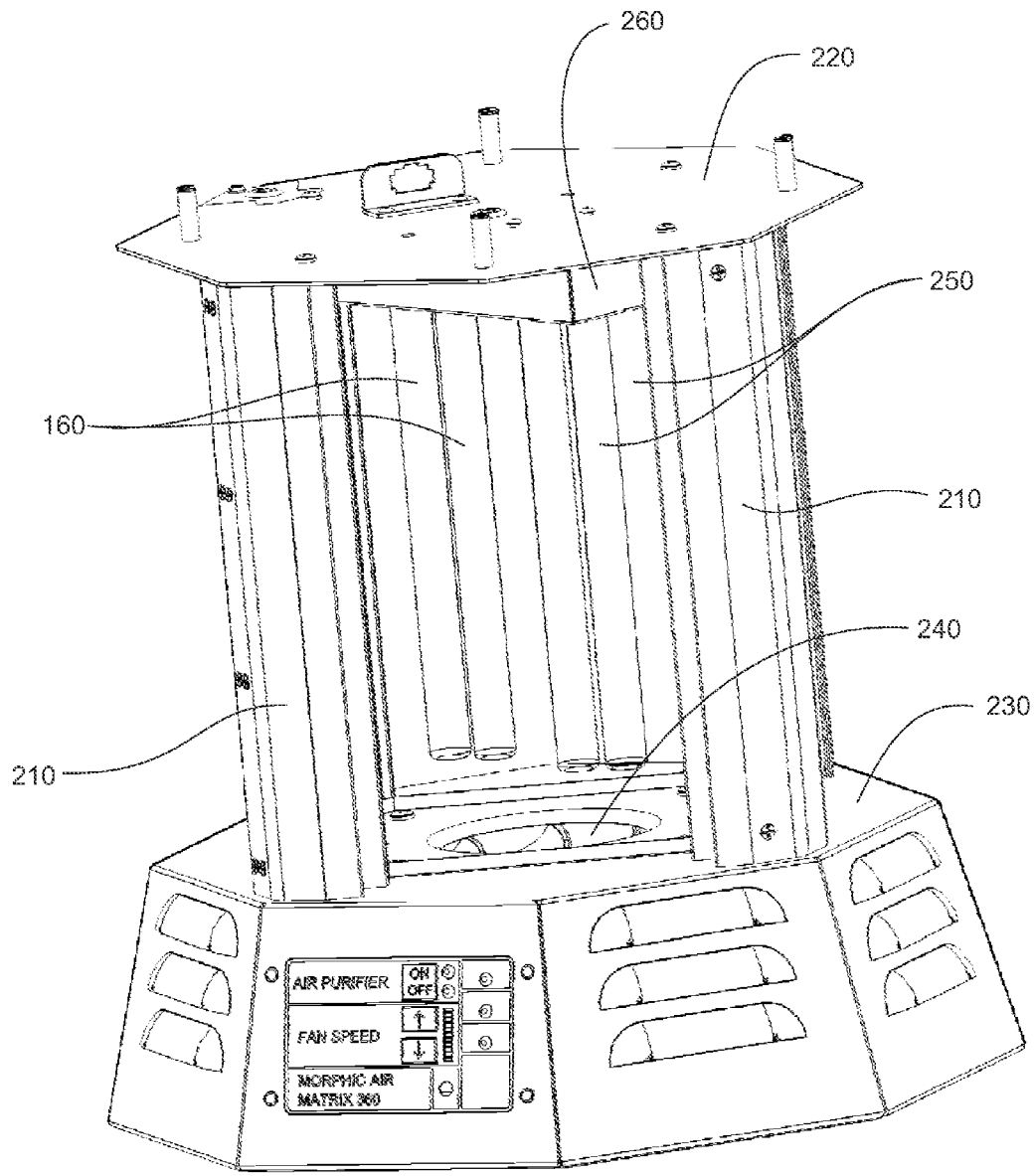
FIG. 10B is a perspective view of the embodiment according to FIG. 10A, missing pre-filters and the four photocatalytic planar elements to better illustrating the UV sources within the core cavity.
Figure 10C:
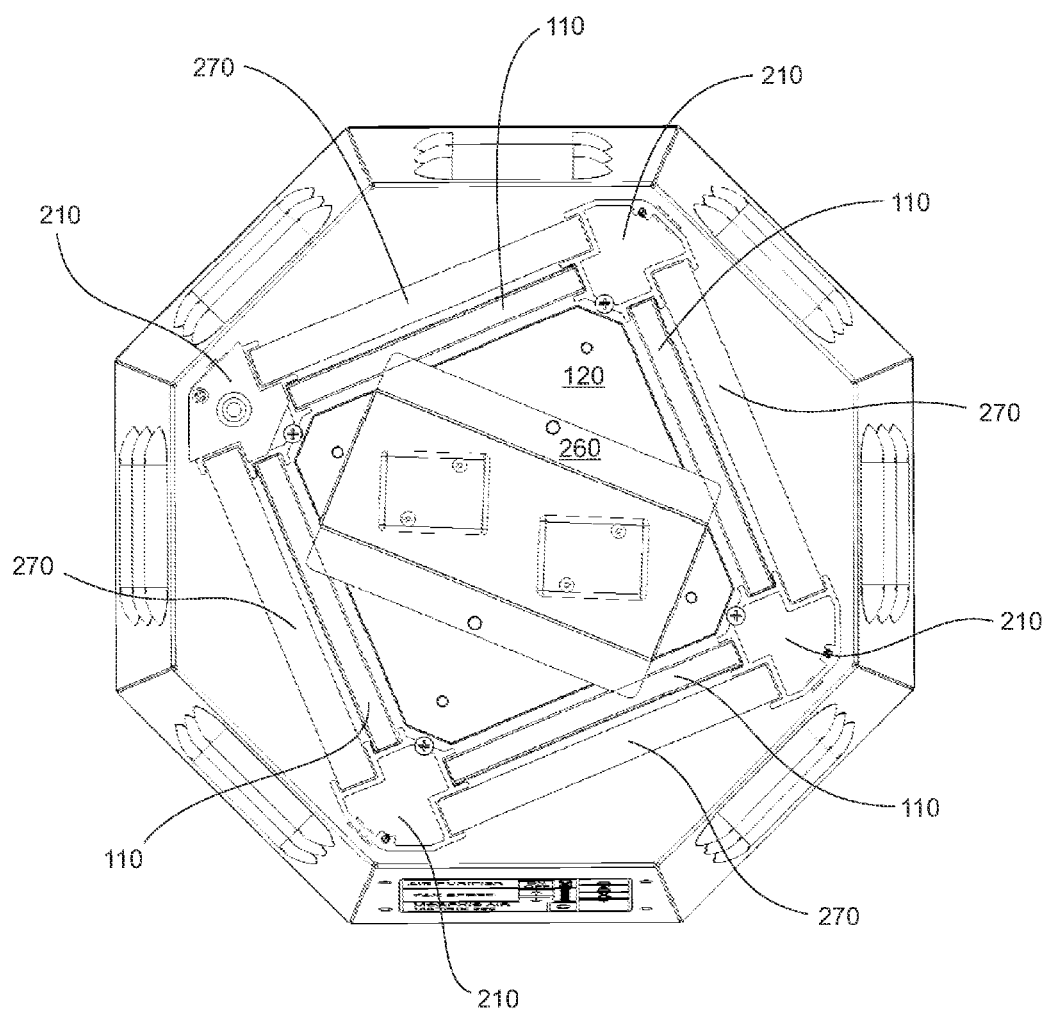
FIG. 10C is top view of the embodiment according to FIG. 10A, illustrating a mounting plate at a top end of the core cavity for supporting the UV sources within the core cavity.

With reference to FIGS. 10A to 10C, an embodiment of the system 100 has four planar elements 110 forming a rectangular core cavity 120 having a square cross-section. Supporting structures, such as posts 210 sealingly arrange the planar elements 110 by interconnecting the planar elements 110 to form the rectangular core cavity 120. The lateral edges of the planar elements sealingly engage the supporting posts 210 while the core cavity 120 is sealed at the top end by a top plate 220. A bottom plate 230 having a port 240, sealing engages the planar elements 110. The core cavity 120 remains open at its bottom end 140 through the port 240. The top plate 220, supporting posts 210, planar elements 110, and ported bottom plate 230 all cooperate to form a sealed air flow path FP for air to travel to through the planar elements 110 and out the port 240.

Referring back to FIGS. 9A and 9B, each planar element 110 defines an upper edge 111, a bottom edge 112, and two opposing lateral edges 113, 114. Each edge has a sealing element, such as a gasket seal, to sealingly engage the top plate 220, supporting posts 210 and the bottom plate 230 ensuring that any air passing by the planar element 110 passes through the element 110, through the UV irradiated interior, into the core cavity 120, to be expelled from the system 200 through the port 240. Once positioned within the system 100, each planar element 110 defines an inside surface 170 facing the UV source 160, and an opposing outside surface 175.

With reference to FIGS. 10B and 10C, a source of UV radiation 160 is disposed within the core cavity 120 to irradiate air travelling within the core cavity 120 as well as the inside surface 170 of the planar elements 110. In embodiments using a substrate being transparent and conductive to UV radiation, the UV radiation upon reaching the inside surface 170 is also refracted and reflected by the quartz fibers to conduct and transmit the UV radiation from the inside surface 170 to the interior for irradiating the interior.

The UV radiation source 160 can be supported by a mounting plate 260 disposed on the top plate 220 or by a mounting plate disposed on the bottom plate (not shown). In a preferred embodiment, the UV source 160 is invertedly supported on the mounting plate 260 to more efficiently use the limited space within the core cavity 120 and to space the UV source 160 away from the port 240, so as not to obstruct the sealed air flow path FP through the port 240.

Figure 11B:
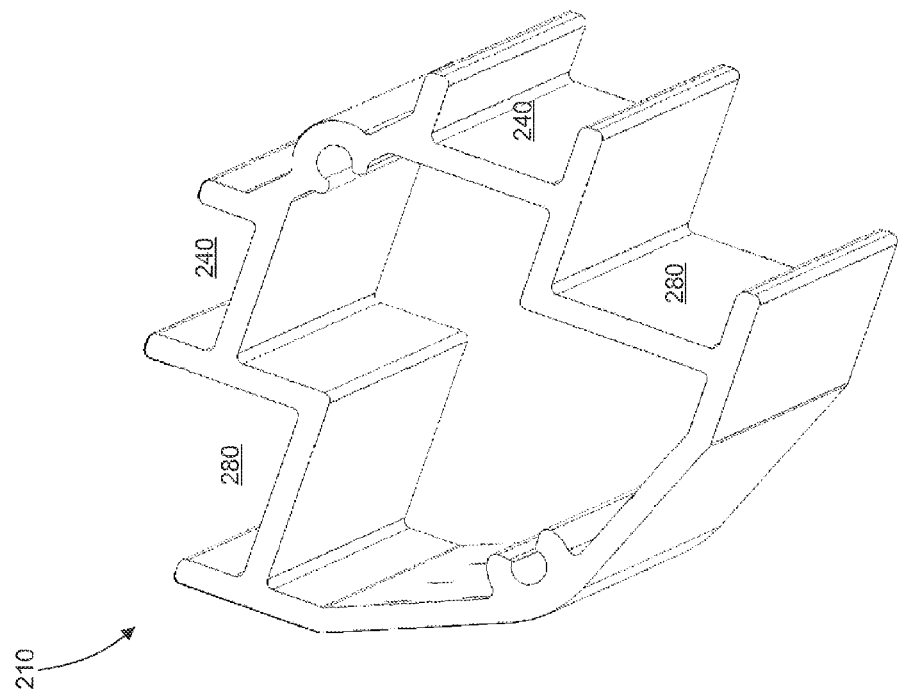
FIG. 11B is a perspective view of the supporting post according to FIG. 11A, illustrating the pre-filter grooves and element grooves.
Figure 11A:
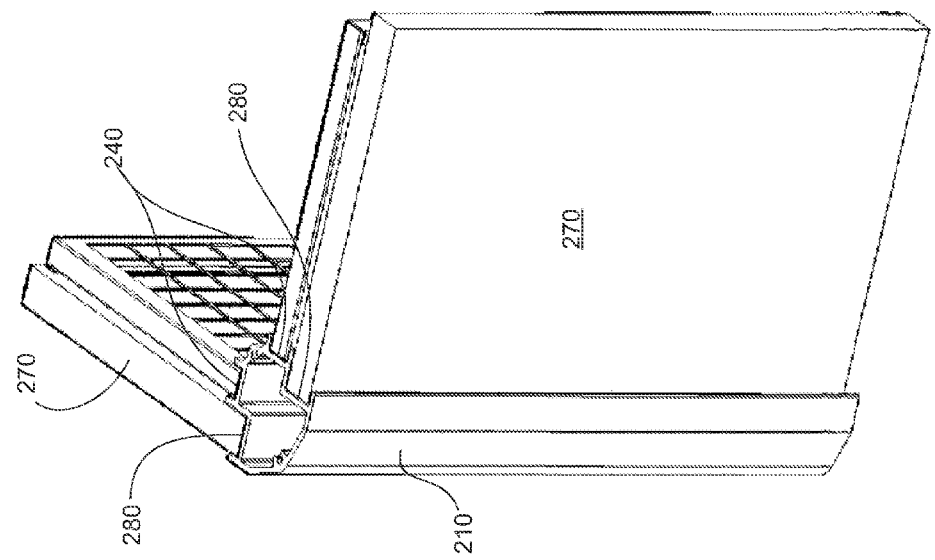
FIG. 11A is a perspective view of an embodiment of the present invention, illustrating a supporting post sealingly engaging a pair of pre-filters and a pair of photocatalytic planar elements.

As shown in FIGS. 11A and 11B, each supporting post 210 has two opposing element grooves 240 for accepting and sealing against the lateral edges 113, 114 of adjoining planar element 110. The supporting posts 210 can be extruded or shaped to accept the lateral edges 113, 114 of each planar element 110. In an embodiment, and as shown in FIGS. 10A to 11B, the system 100 comprises a pre-filter, such as a particulate filter 270 adjacent to the outside surface 175 of each planar element 110, for removing particulates entrained in the air. The particulate filter 270 is positioned to intercept the air travelling along the flow path FP before the air enters the interior of the planar elements 110. Removal of entrained particulates extends the functional life of the planar elements 110 as the planar elements 110 would not become unnecessarily clogged with particulates. As shown in FIGS. 11A and 11B, in such an embodiment, the supporting posts 210 are further fit with opposing particulate filter grooves 280 for accepting and sealingly engaging lateral edges of adjoining particulate filter 270 to preserve the sealed flow path FP. Each planar element 110 is matched with a planar particulate filter 270.

In another embodiment, a pressure sensor (not shown) can be utilized to monitor the pressure within the core cavity 120. As air is drawn into the core cavity 120, a lower pressure is formed therein. Over a period of use, physical contaminants, microbes and/or volatile contaminants can build up on the pre-filters 270 and the planar elements 110 to interfere with the amount of air flowing through the system 100. This interference of air flowing through the system 100 can result in a further lowering of the pressure within the core cavity 120, below a threshold pressure, which would be indicia for replacement of the particulate filters 270 and/or planar elements 110.

In another embodiment, the top plate 130 can be indexed to the posts to ensure that it is sealed against the top edges 111 of each of the planar elements 110 in a specific orientation, providing proper alignment of the top plate 130, the mounting plate 260, and the inverted UV source 160 within the core cavity 120.

Figure 12:
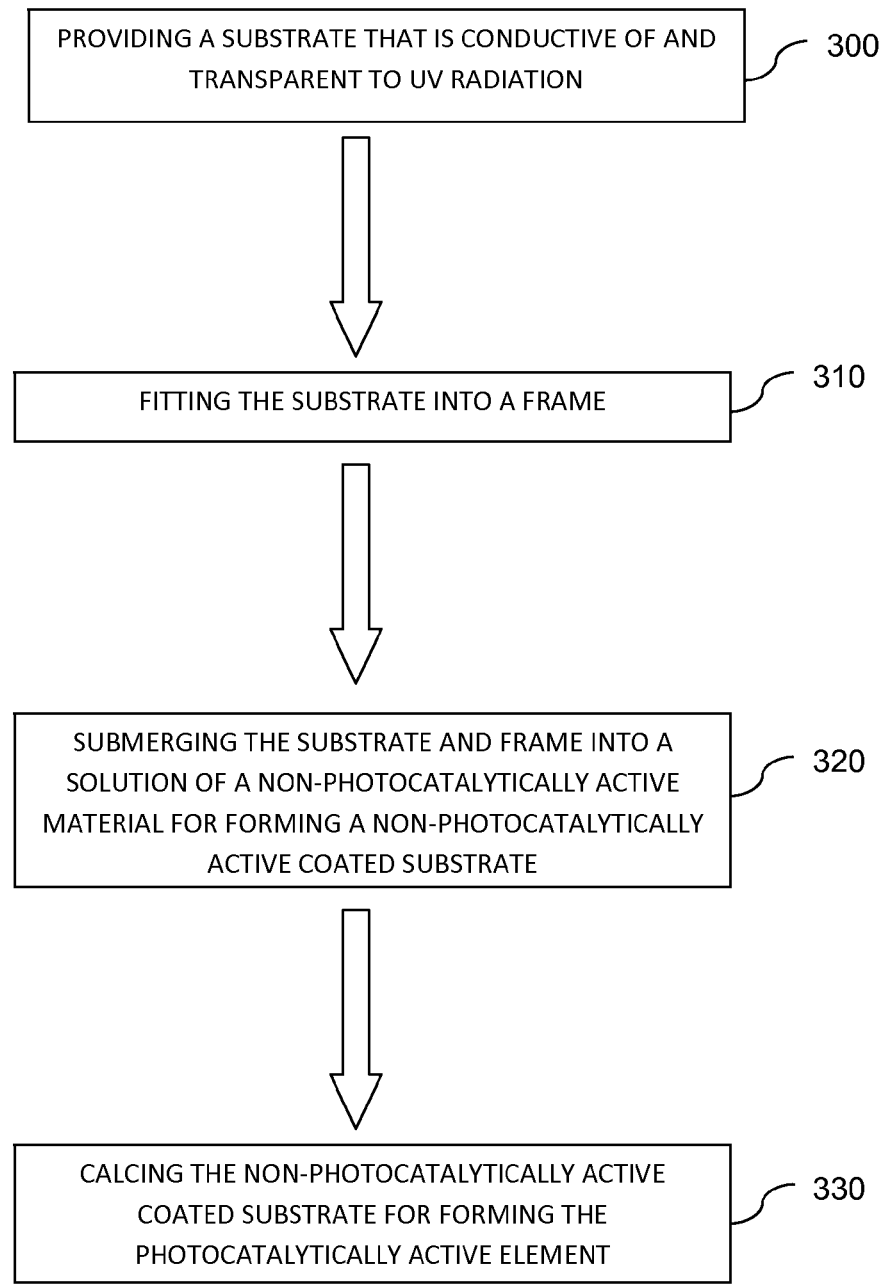
FIG. 12 is a flow chart of an embodiment of the present invention illustrating a method of manufacturing a photocatalytic planar element to be used in cooperation with two or more planar elements sealingly arranged to form a core cavity for forming a sealed flow path.

With reference to FIG. 12, a method for manufacturing a planar photocatalytic element is illustrated. A substrate is provided 300, such as quartz fibers, that is conductive of and transparent to UV radiation. The substrate is secured of fit 310 to a frame. The substrate and frame is then dipped or submerged 320 in a solution containing a non-photocatalytic material, such as peroxotitanic acid, for forming a non-photocatalytically active coated substrate. Once submerged, the peroxotitanic acid coats or wets the quartz fibers. The peroxotitanic acid-coated quartz fibers are then calcined 330 to form a photocatalytically active element 110.

More specifically, an appropriately sized piece of quartz wool 200 is cut from a larger mat of QUARTZEL®. The quartz wool mat, when rolled for shipping and storage purposes, has a mat thickness of about ¼ inches. Once unrolled, the quartz wool mat can expand to about 5 inches in mat thickness.

As shown in FIG. 9C, the cut piece of quartz wool 200 is secured within frame 180 by a screen 190. In the embodiment illustrated, as the frame 180 has a thickness less than that of the expanded piece of quartz wool 200, the expanded piece of quartz wool 200 can be sandwiched between the frame 180 and screen 190 and then compressed using known methods.

For example, in one embodiment, a frame 180 about one inch thick can be placed on top of a vacuum table, such as those commonly used in vacuum forming processes (vacuforming). The 5 inch thick expanded piece of quartz wool 200 is sandwiched in between the frame 180 and screen 190 and is induced or drawn to the frame 180 by a suction provided by the vacuum table. The screen 190 is then secured to the frame 180 to contain the quartz wool 200 within the frame 180. The screen 190 can be secured to the frame 180 by any known securing means, such as by rivets or spring clips.

The frame 180, substrate 200, and screen 190 are dipped or submerged in a solution containing a material that is not photocatalytically active, such as peroxotitanic acid, for coating or wetting the individual quartz fibers. The wet substrate is then dried to form a dry coat of peroxotitanic acid coating the quartz fibers, forming a non-photocatalytically active element. In one embodiment, the drying can be performed by using the vacuum table to speed the drying to form the dry coat.

The non-photocatalytically active element is then baked to form the photocatalytically active planar element 110. The non-photocatalytically active material, such as peroxotitanic acid, is converted to an active photocatalyst, such as anatase titanium dioxide, by baking it at a temperature ranging from about 300 degrees Celsius to about 700 degrees Celsius. The baking process or calcination of the dried peroxotitianic acid, causes the dried peroxotitanic acid to convert to a photocatalytically active anatase form of titanium dioxide strongly bonded to the quartz fibers. In a preferred embodiment, the baking or calcination of the dried peroxotitanic acid is at about 500 degrees Celsius.

Applicant notes that titanium dioxide can exist in three morphologies including brookite, anatase, and rutile. Calcination of peroxotitanic acid above 700 degrees Celsius will cause all brookite and anatase forms of titanium dioxide to form into rutile titanium dioxide. While rutile titanium dioxide is the most thermodynamically stable of the three morphologies, it is also has the least photocatalytic activity. Thus, calcination of the peroxotitanic acid should minimize the formation of rutile titanium dioxide.

The active element produced in this manner is advantageous over an active panel manufactured in accordance to FIG. 4. The bonding strength (believed to be predominantly van der Waals forces) between the anatase titanium dioxide and the quartz fibers when formed by calcining is greater than the bonding strength between the anatase titanium dioxide-quartz fiber and the substrate when bound together by dried peroxotitanic acid acting as an inorganic binder.

In another embodiment, the wet panel can be baked directly without drying. In such a case, the calcination process takes a longer as residual water must be driven off before the peroxotitanic acid can covert to the photocatalytically active anatase form of titanium dioxide.

The embodiments of the invention for which an exclusive property or privilege is claimed are defined as follows:

1. A method of manufacturing one or more photocatalytically active elements for use in a germicidal irradiation system, the one or more active elements forming a sealed flow path for passing pre-filtered air through the one or more photocatalytically active elements and thereafter through a UV-irradiated core cavity defined by the one or more elements, the core cavity having a sealed top end and an open bottom end for discharging treated air therefrom, the method of manufacturing each photocatalytically active element comprising:

providing a plurality of tangled, non-oriented quartz fibers, each fiber having a fiber diameter equal to or less than about 9 microns, for forming a medium conductive of and transparent to UV radiation;

supporting the medium by sandwiching the medium within mesh into a planar frame, the medium having a flow path therethrough from a UV core cavity side and a sufficient thickness of the medium to provide for near complete extinction of the UV radiation therethrough without restricting air flow;

submerging the frame, mesh and medium in a solution containing non-photocatalytically active material for coating the non-oriented fibers in the medium; and calcining the coated medium while supported in the frame and mesh for converting the non-photocatalytically active material to an active photocatalyst bound to and coating the non-oriented fibers in the medium for forming each photocatalytically active element.

2. The method of claim 1 further comprising drying the non-photocatalytically active coating prior to calcining the coated medium.

3. The method of claim 1 wherein the non-photocatalytically active material is peroxotitanic acid.

4. The method of claim 3 wherein calcining of the coated medium comprises converting the peroxotitanic acid into anatase titanium dioxide.

5. The method of claim 1 wherein calcining of the coated medium further comprises baking at a temperature range of about 300 degrees Celsius to about 700 degrees Celsius.

6. The method of claim 5 wherein calcining of the coated medium further comprises baking at a temperature of about 500 degrees Celsius.

7. The method of claim 1 wherein the tangled, non-oriented fibers are quartz fibers and a photocatalyst coating coverage density of the quartz fibers in the medium within each of the one or more elements can be determined by the equation:

Coating Density=PC/A wherein PC is a weight of the active photocatalyst applied to the medium surface A which can be determined by the equation $PC=(S_W-S_D)*C/\rho$ (in grams), where $S_W$ is a weight of the medium wet with the solution, $S_D$ is a weight of dry medium used, C is a concentration of the non-photocatalytically active material (g/mL) in the solution, and $\rho$ is a density of the solution.

8. The method of claim 1, further comprising compressing said medium within the mesh for supporting the medium within the frame.

9. The method of claim 1 further comprising:

obtaining a first weight of the medium before submerging in said solution;

obtaining a second weight of the medium after submerging in said solution; and calculating coating coverage based on said first weight and second weight.

* * * * *